United States Patent [19]
Burbank et al.

[11] Patent Number: 5,980,469
[45] Date of Patent: Nov. 9, 1999

[54] METHOD AND APPARATUS FOR AUTOMATED BIOPSY AND COLLECTION OF SOFT TISSUE

[75] Inventors: Fred H. Burbank, San Juan Capistrano; Thomas J. Fogarty, Portola Valley; Wayne E. Manska, Anaheim; Mark A. Ritchart, Murrieta; Timothy J. Ryan, Los Gatos, all of Calif.; Elias A. Zerhouni, Baltimore, Md.

[73] Assignee: Ethicon Endo-Surgery, Inc., Cincinnati, Ohio

[21] Appl. No.: 09/004,782

[22] Filed: Jan. 9, 1998

Related U.S. Application Data

[60] Continuation of application No. 08/645,225, May 13, 1996, Pat. No. 5,775,333, which is a division of application No. 08/217,246, Mar. 24, 1994, Pat. No. 5,526,822.

[51] Int. Cl.⁶ .................................................. A61B 10/00
[52] U.S. Cl. ........................................................... 600/567
[58] Field of Search .................................... 600/564–567; 606/167, 170

[56] References Cited

U.S. PATENT DOCUMENTS

| | | |
|---|---|---|
| Re. 33,258 | 7/1990 | Onik et al. . |
| Re. 34,056 | 9/1992 | Lindgren et al. . |
| 2,705,949 | 4/1955 | Silverman . |
| 2,919,692 | 1/1960 | Ackermann ............................. 128/754 |
| 3,590,808 | 7/1971 | Muller . |
| 3,606,878 | 9/1971 | Kellogg, Jr. . |
| 3,732,858 | 5/1973 | Banko ..................................... 128/753 |
| 3,734,099 | 5/1973 | Bender et al. . |
| 3,844,272 | 10/1974 | Banko . |
| 3,929,123 | 12/1975 | Jamshidi . |
| 4,099,518 | 7/1978 | Baylis et al. . |
| 4,200,106 | 4/1980 | Douvas et al. . |
| 4,203,444 | 5/1980 | Bonnell et al. . |
| 4,210,146 | 7/1980 | Banko . |
| 4,243,048 | 1/1981 | Griffin .................................... 128/751 |
| 4,306,570 | 12/1981 | Matthews ............................... 600/567 |

(List continued on next page.)

FOREIGN PATENT DOCUMENTS

| | | |
|---|---|---|
| 0378692 | 7/1990 | European Pat. Off. . |
| 0442851 | 8/1991 | European Pat. Off. . |
| 935625 | 5/1955 | Germany . |
| WO 93/14707 | 8/1993 | WIPO . |
| WO 93/22972 | 11/1993 | WIPO . |

OTHER PUBLICATIONS

ASAP™—Automatic Soft Biopsys System®—Boston Scientic Corp; 1992; 2 pp.
"New? from Bard® Radiology—When It Comes To Core Samples, I Demand Accuracy and Consistency for All my Patients." Bard Radiology; 1987; 4 pp.
"Nucleotome® System—Automated Percutaneous Lumbar Discectomy™" Surgical Dynamics™; 1990; 4 pp.

*Primary Examiner*—Max Hindenburg
*Attorney, Agent, or Firm*—Stout, Uxa, Buyan & Mullins, LLP; Donald E. Stout

[57] ABSTRACT

A method and device for the automated biopsy and collection of soft tissue having a piercing needle with a receiving port to trap tissue prior to cutting. A motor drive directs and positions the tissue receiving port at a lesion site in arbitrary positions about and along the longitudinal axis of the device. A cutter advances into the receiving chamber and severs tissue which has prolapsed into the receiving port. The severed tissue is then removed from the receiving port without removing the piercing needle receiving port from the lesion site, thus allowing for the accurate, rapid removal of an arbitrary number of core samples with only one insertion. A tissue sample cassette provides storage for the samples as well as a means for coding and decoding the location from which the samples were obtained. Together, these features allow for more accurate and complete sampling of large lesions, for the complete removal of small lesions or removal of other tissue for a variety of reasons.

17 Claims, 20 Drawing Sheets

U.S. PATENT DOCUMENTS

| | | | |
|---|---|---|---|
| 4,461,305 | 7/1984 | Cibley | 128/754 |
| 4,517,977 | 5/1985 | Frost | 604/22 |
| 4,600,014 | 7/1986 | Beraha . | |
| 4,644,951 | 2/1987 | Bays . | |
| 4,651,753 | 3/1987 | Lifton . | |
| 4,681,123 | 7/1987 | Valtchev . | |
| 4,699,154 | 10/1987 | Lindgren | 128/754 |
| 4,702,260 | 10/1987 | Wang | 128/753 |
| 4,702,261 | 10/1987 | Cornell et al. | 128/754 |
| 4,708,147 | 11/1987 | Haaga | 128/753 |
| 4,729,764 | 3/1988 | Gualtier . | |
| 4,733,671 | 3/1988 | Mehl | 128/754 |
| 4,735,215 | 4/1988 | Goto et al. | 128/754 |
| 4,735,245 | 4/1988 | Goto et al. | 128/754 |
| 4,781,202 | 11/1988 | Janese . | |
| 4,844,088 | 7/1989 | Kambin | 128/753 |
| 4,850,373 | 7/1989 | Zatloukal et al. . | |
| 4,893,635 | 1/1990 | de Groot et al. | 128/754 |
| 4,919,146 | 4/1990 | Rhinehart et al. . | |
| 4,924,878 | 5/1990 | Nottke . | |
| 4,940,061 | 7/1990 | Terwilliger et al. . | |
| 4,944,308 | 7/1990 | Akerfeldt | 128/751 |
| 4,958,625 | 9/1990 | Bates et al. . | |
| 4,966,583 | 10/1990 | Debbas | 604/98 |
| 4,971,067 | 11/1990 | Bolduc et al. | 182/751 |
| 4,976,269 | 12/1990 | Mehl . | |
| 4,991,592 | 2/1991 | Christ | 128/754 |
| 5,005,585 | 4/1991 | Mazza | 128/754 |
| 5,031,634 | 7/1991 | Simon . | |
| 5,048,538 | 9/1991 | Terwilliger et al. . | |
| 5,108,381 | 4/1992 | Kolozsi | 604/319 |
| 5,111,828 | 5/1992 | Kornberg et al. | 128/754 |
| 5,121,751 | 6/1992 | Panalletta | 600/567 |
| 5,125,413 | 6/1992 | Baran . | |
| 5,133,359 | 7/1992 | Kedem | 128/754 |
| 5,133,360 | 7/1992 | Spears | 128/754 |
| 5,174,300 | 12/1992 | Bales et al. . | |
| 5,183,052 | 2/1993 | Terwilliger . | |
| 5,183,054 | 2/1993 | Burkholder et al. . | |
| 5,188,118 | 2/1993 | Terwilliger . | |
| 5,195,533 | 3/1993 | Chin et al. . | |
| 5,197,484 | 3/1993 | Kornberg et al. . | |
| 5,217,458 | 6/1993 | Parins . | |
| 5,217,479 | 6/1993 | Shuler . | |
| 5,224,470 | 7/1993 | Schnepp-Pesch et al. . | |
| 5,224,488 | 7/1993 | Neuffer | 128/751 |
| 5,234,000 | 8/1993 | Hakky et al. . | |
| 5,240,011 | 8/1993 | Assa . | |
| 5,243,994 | 9/1993 | Ranalletta . | |
| 5,249,583 | 10/1993 | Mallaby . | |
| 5,255,688 | 10/1993 | Gilliard . | |
| 5,282,476 | 2/1994 | Terwilliger | 128/753 |
| 5,284,156 | 2/1994 | Schramm et al. | 600/567 |
| 5,301,684 | 4/1994 | Ogirala | 128/754 |
| 5,313,958 | 5/1994 | Bauer | 128/754 |
| 5,316,013 | 5/1994 | Striebal, II et al. | 128/754 |
| 5,320,110 | 6/1994 | Wang | 128/753 |
| 5,324,300 | 6/1994 | Elias et al. | 606/180 |
| 5,333,619 | 8/1994 | Burgio | 128/754 |
| 5,335,672 | 8/1994 | Bennett | 128/754 |
| 5,336,176 | 8/1994 | Yoon | 604/51 |
| 5,341,816 | 8/1994 | Allen | 128/754 |
| 5,348,022 | 9/1994 | Leigh et al. | 128/753 |
| 5,353,804 | 10/1994 | Kornberg et al. | 128/754 |
| 5,368,045 | 11/1994 | Clement et al. | 128/754 |
| 5,394,887 | 3/1995 | Haaga . | |
| 5,560,373 | 10/1996 | DeSantis . | |

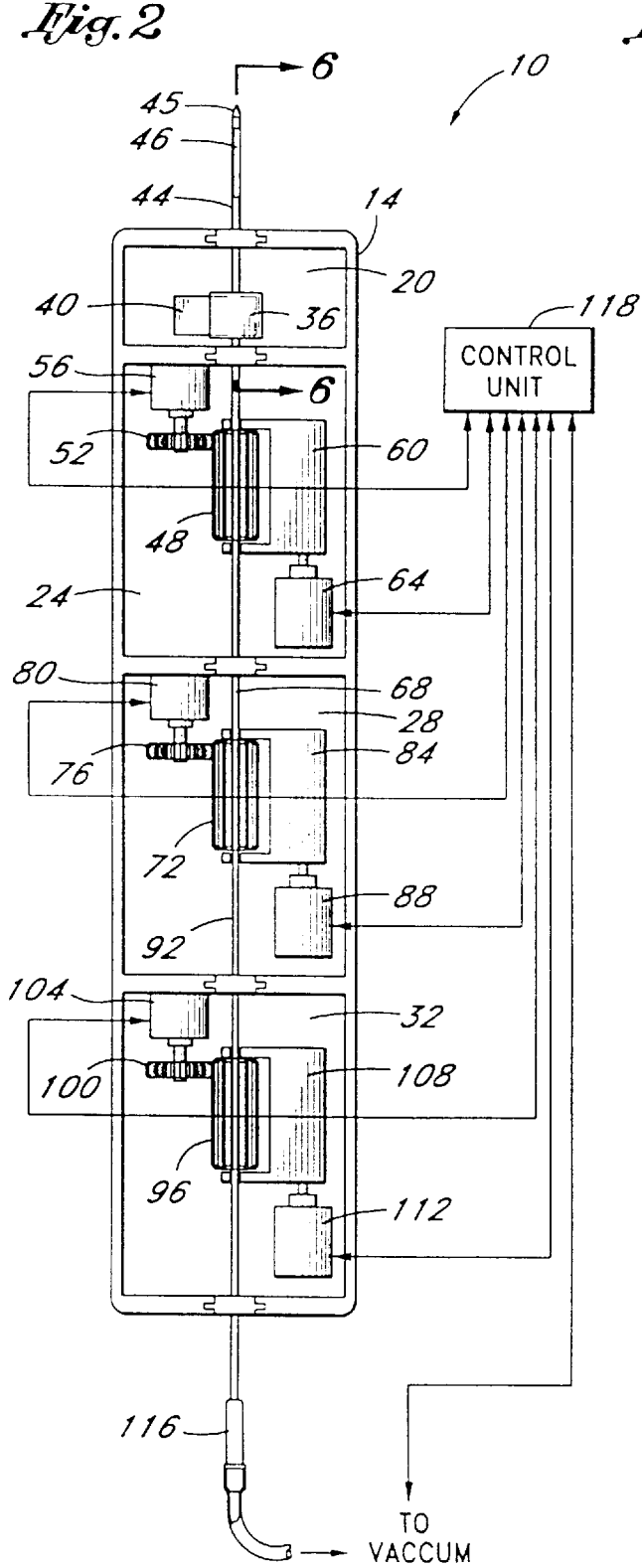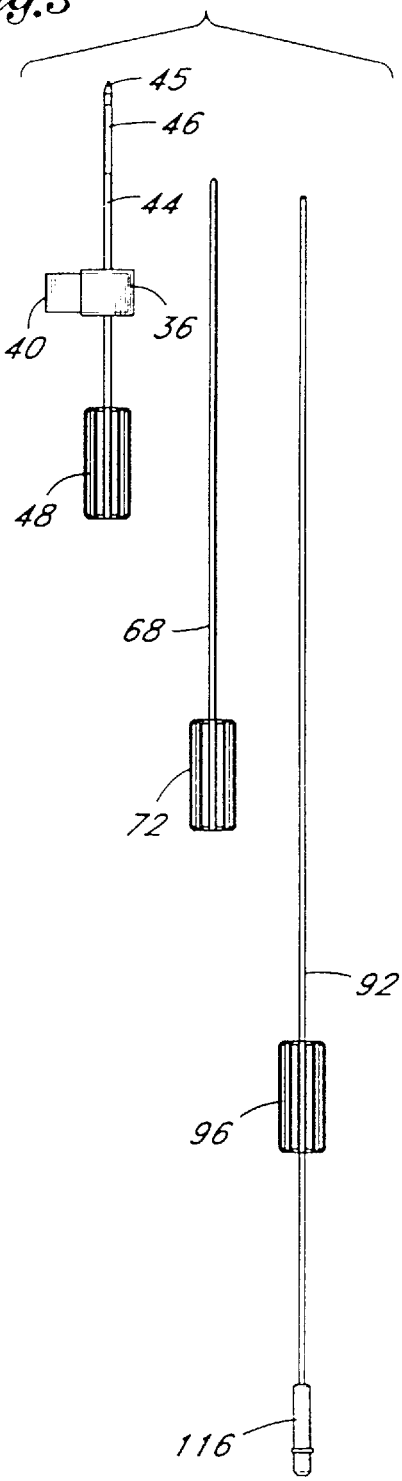

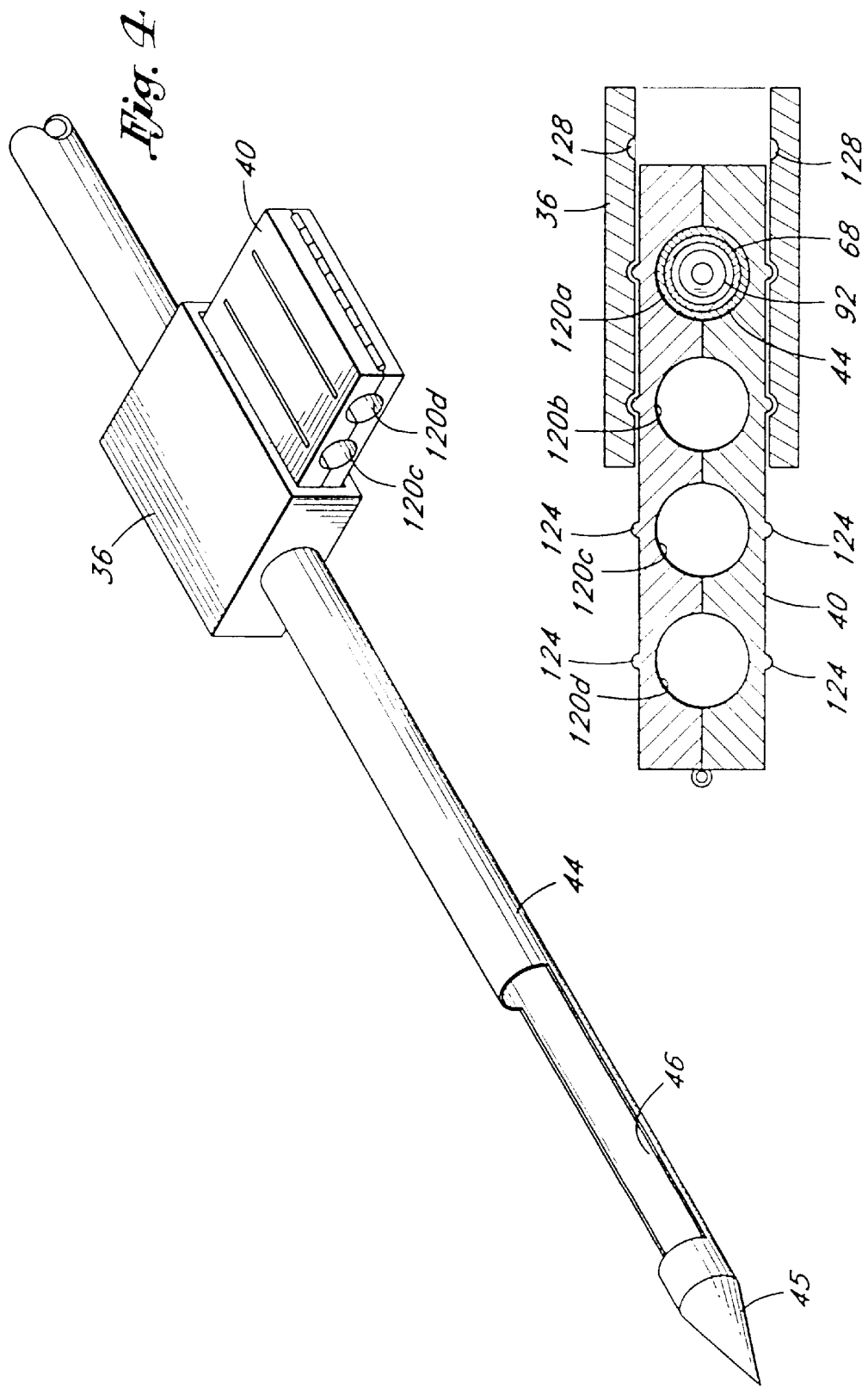

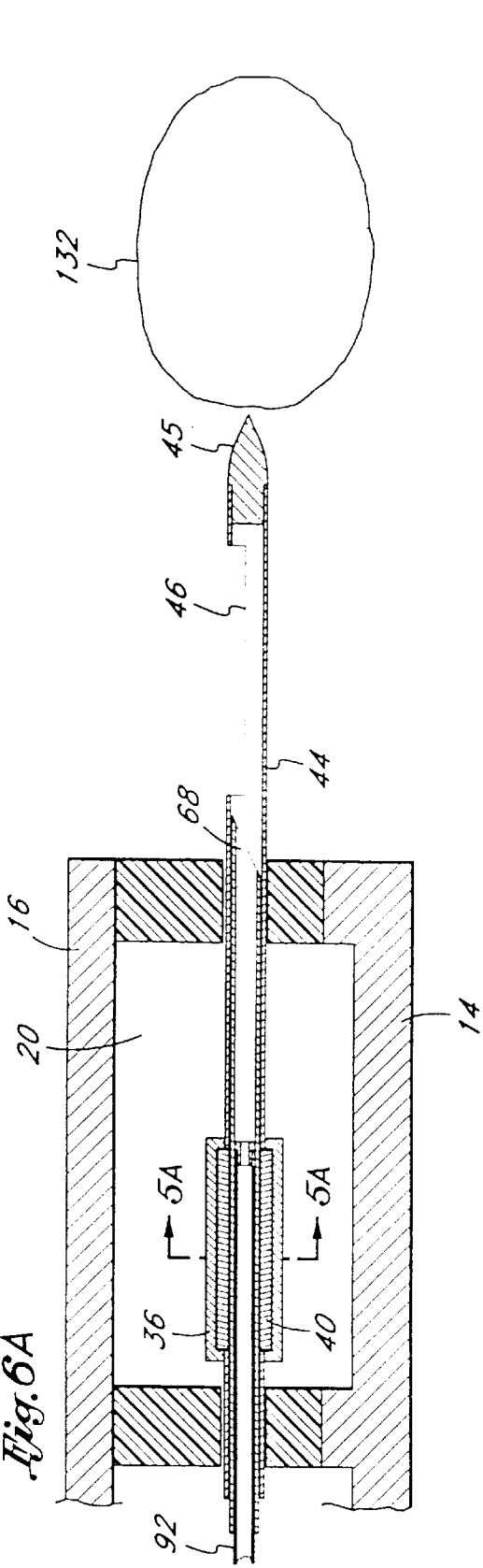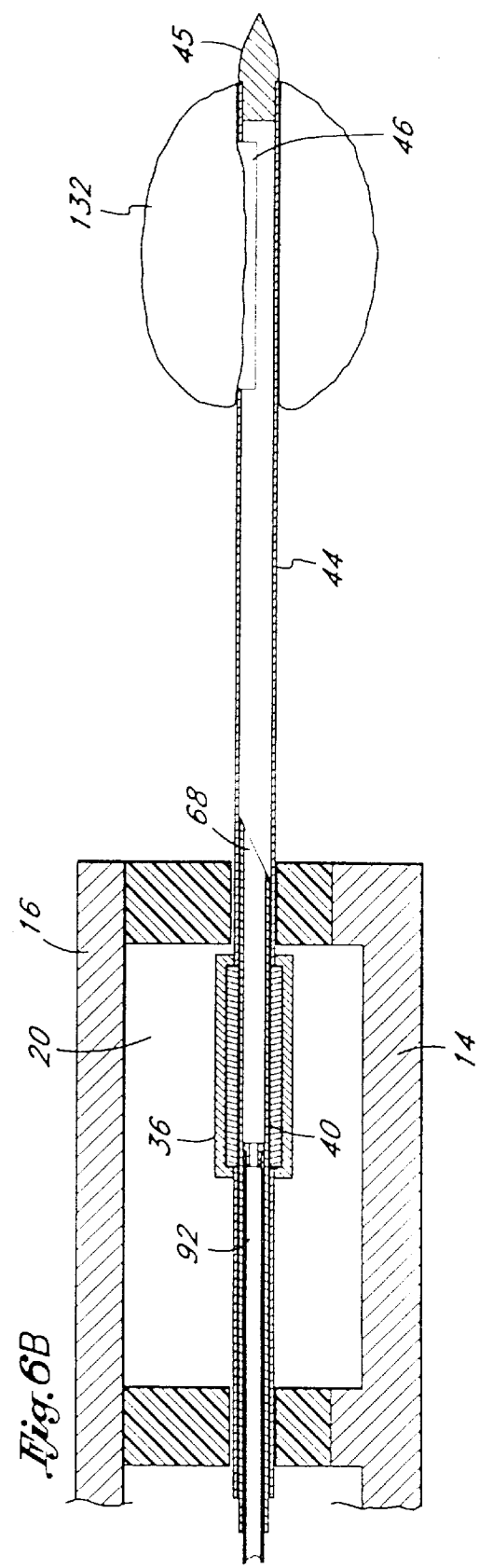

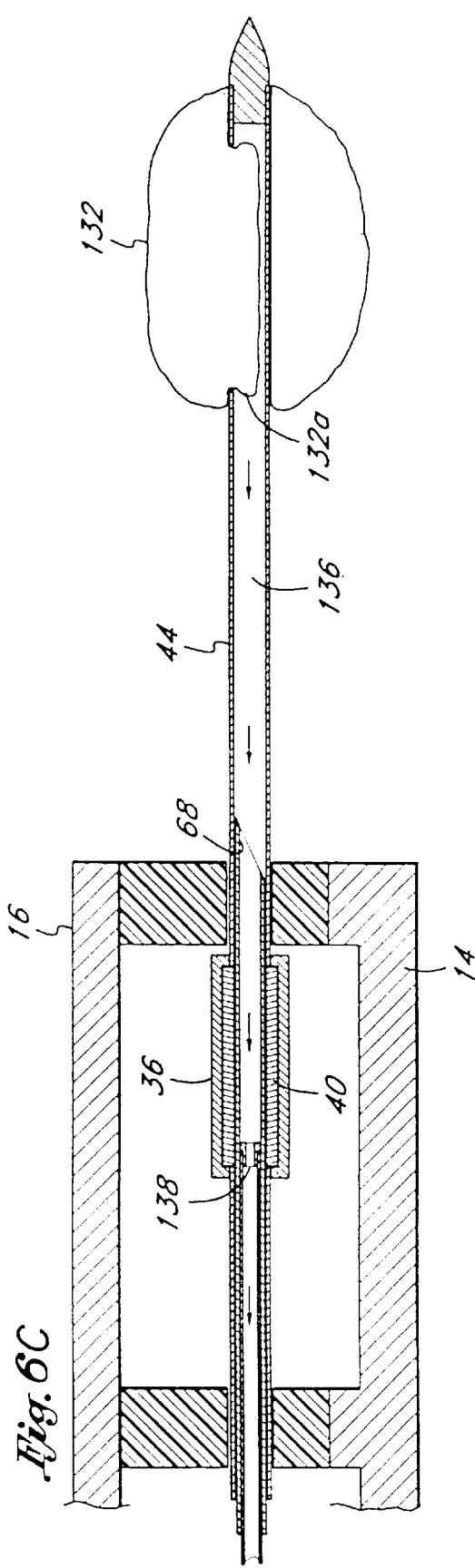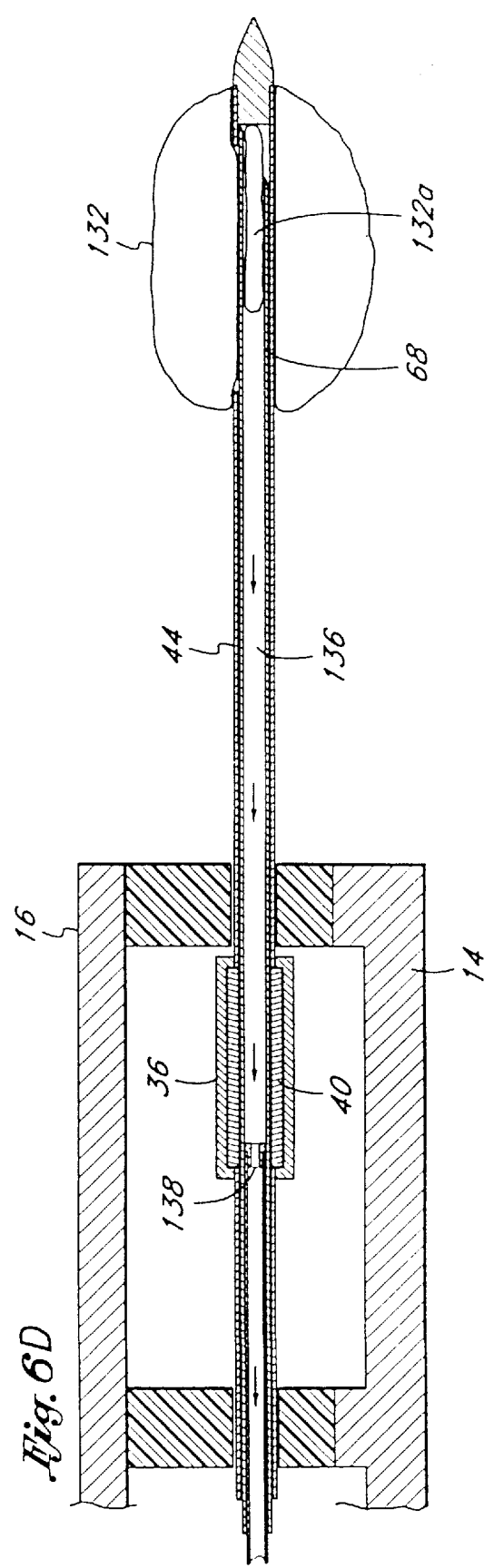

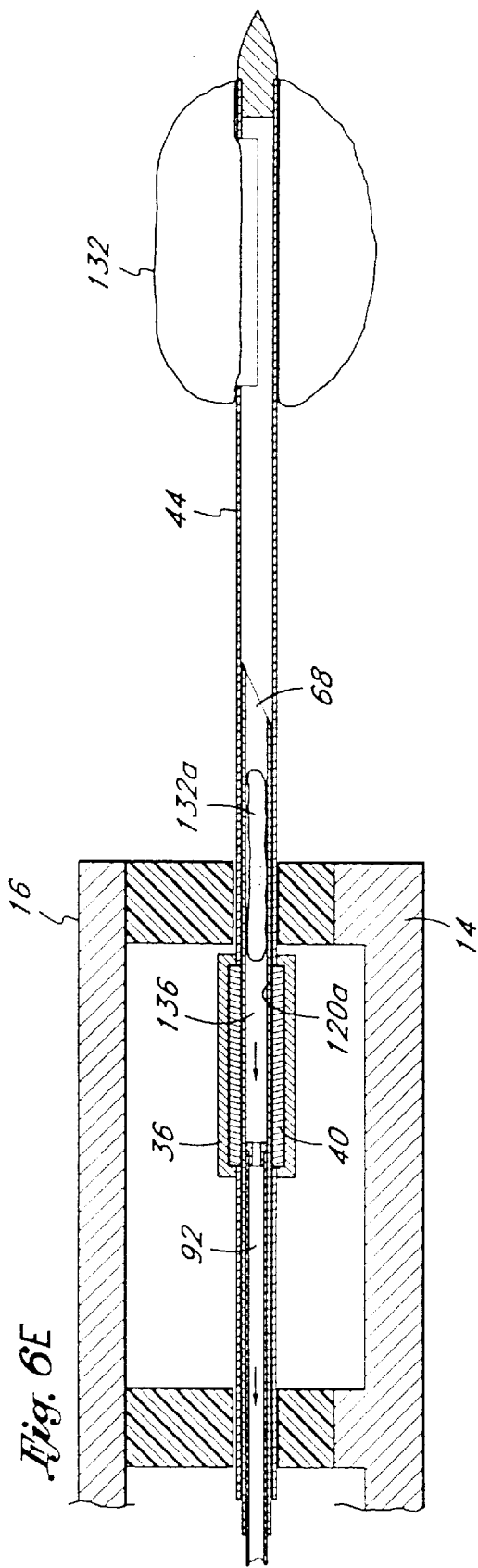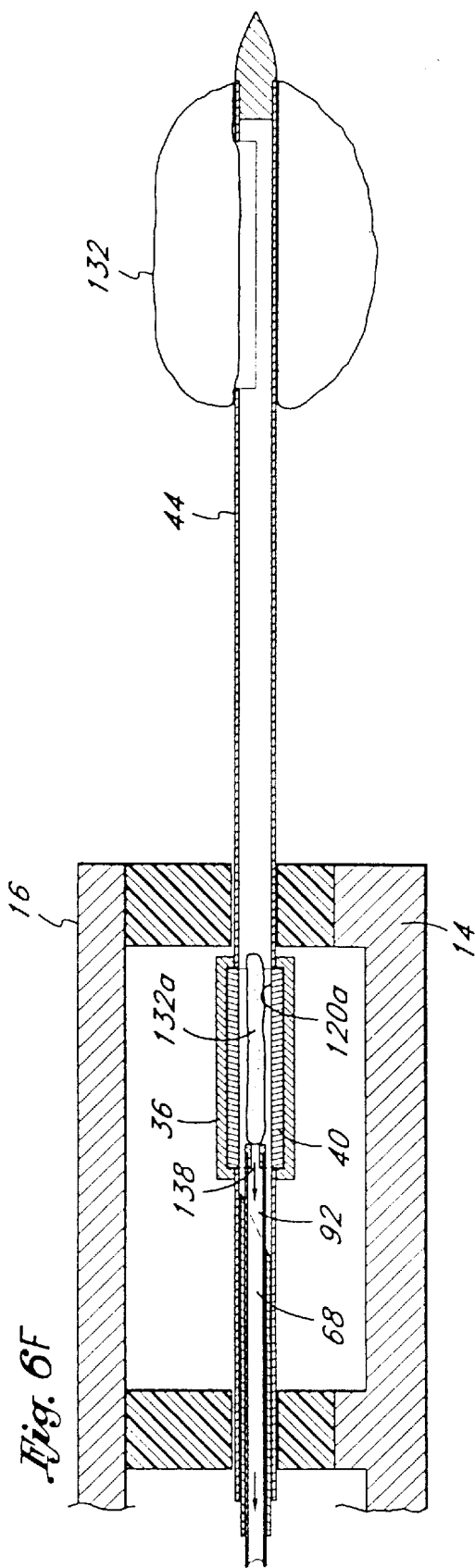

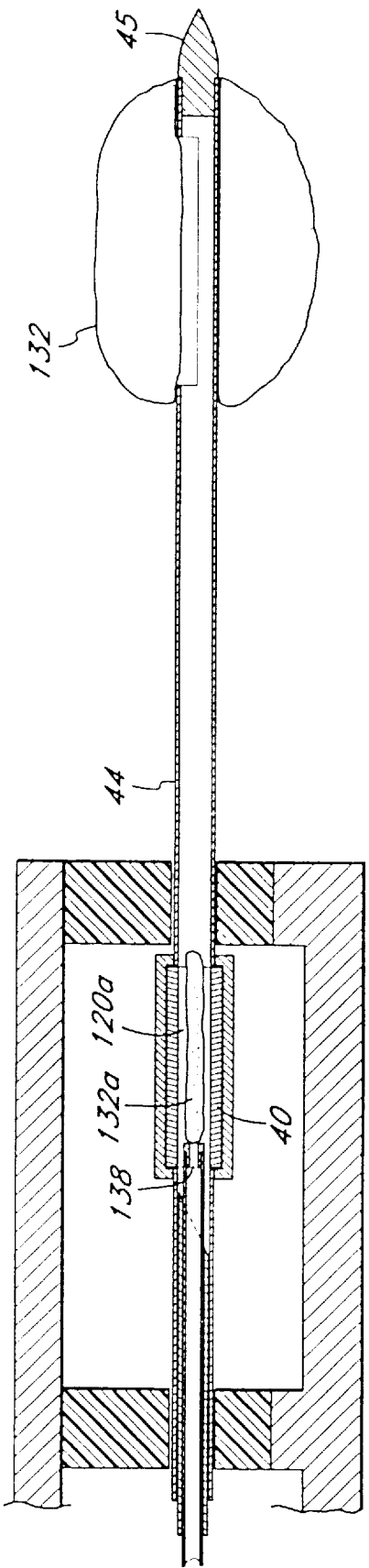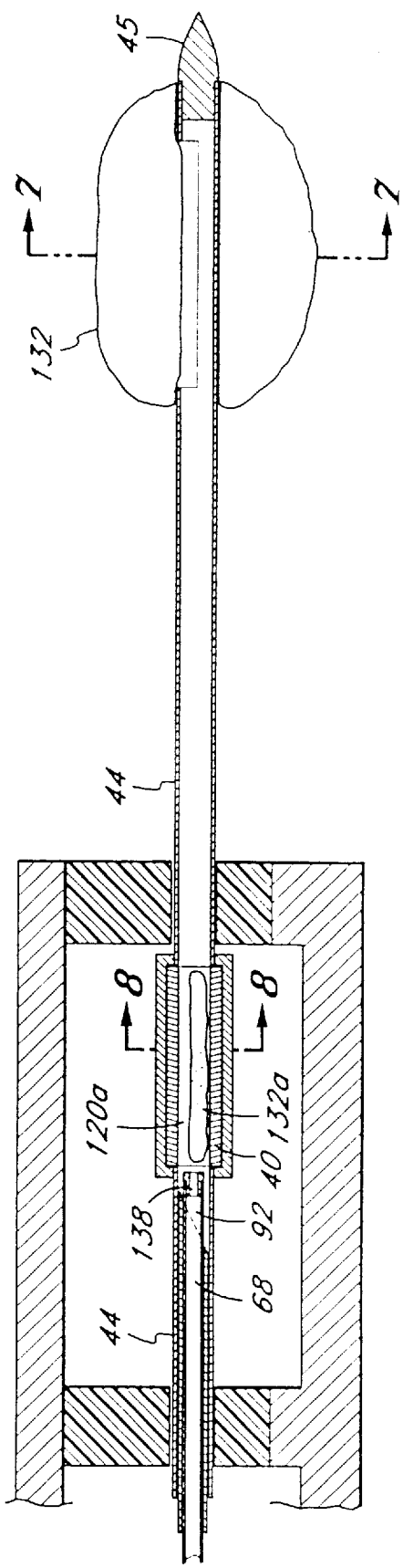

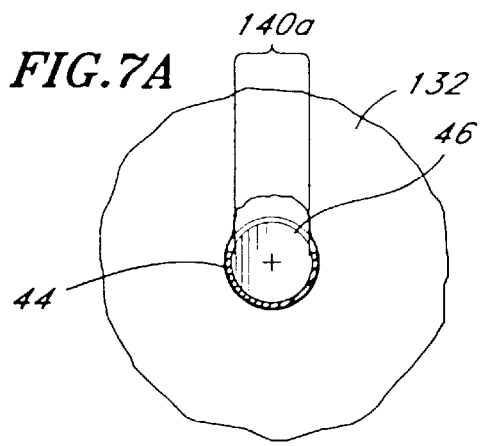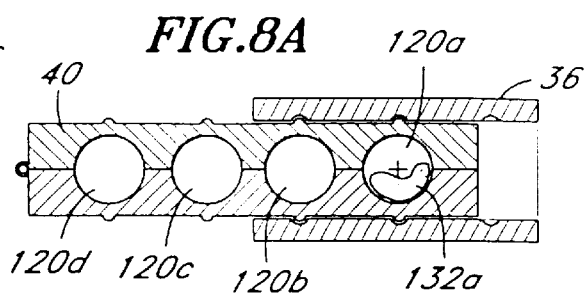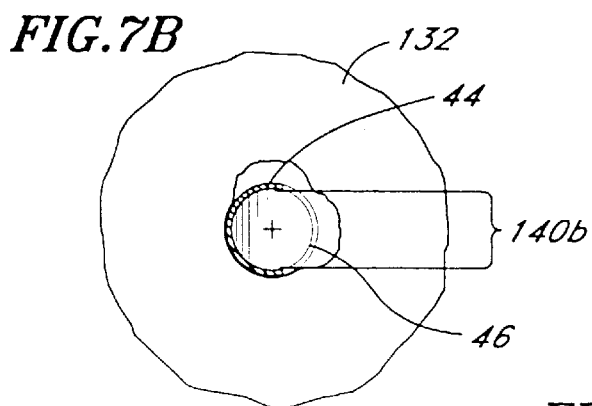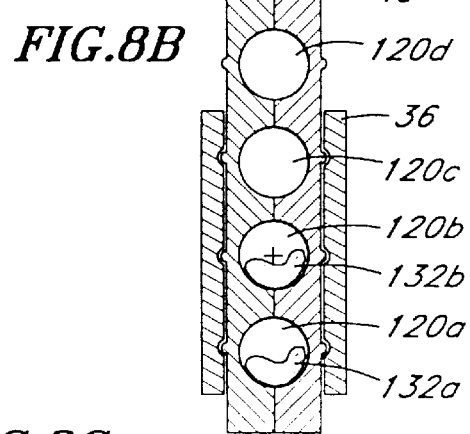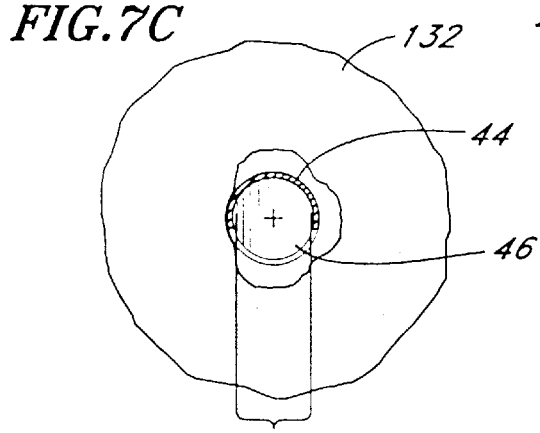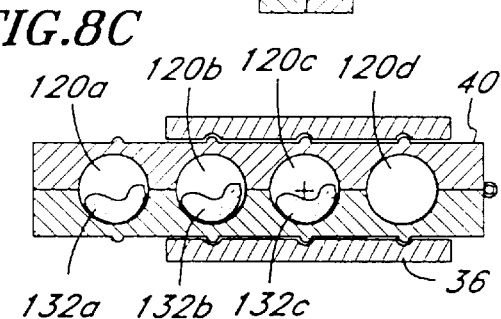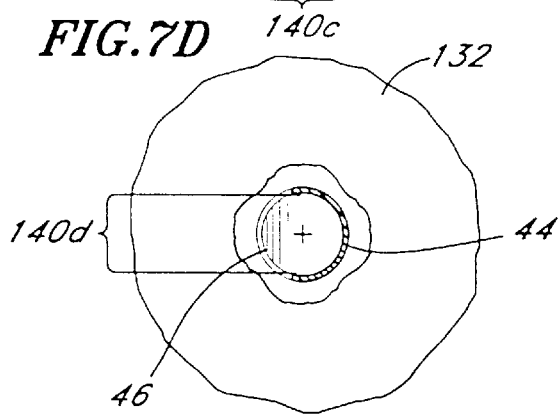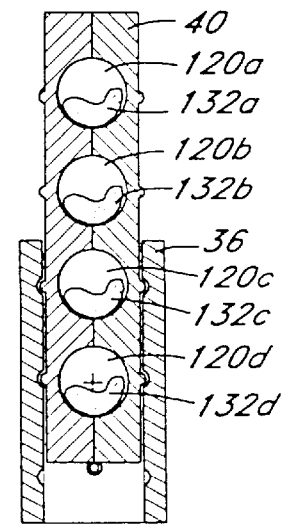

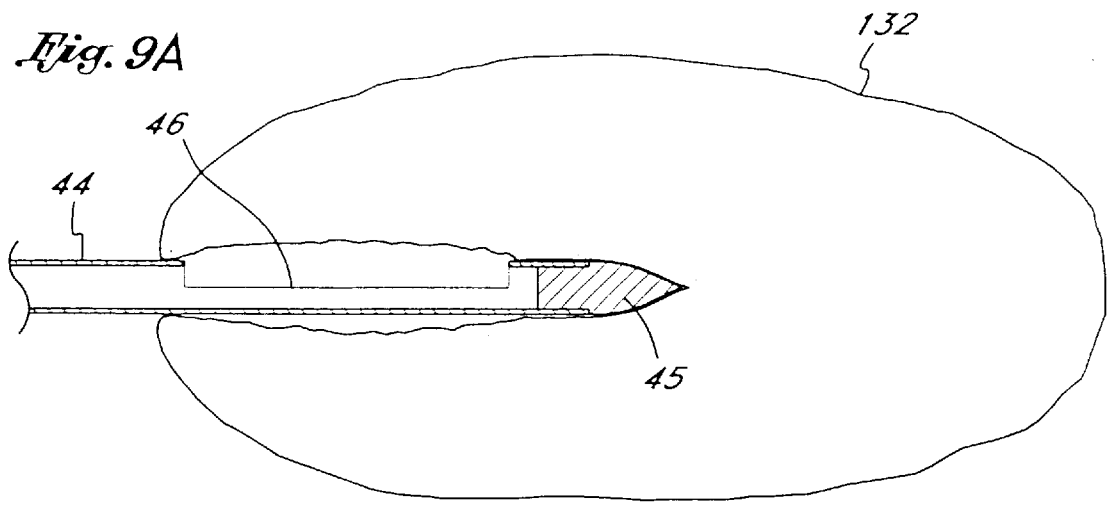
Fig. 9A
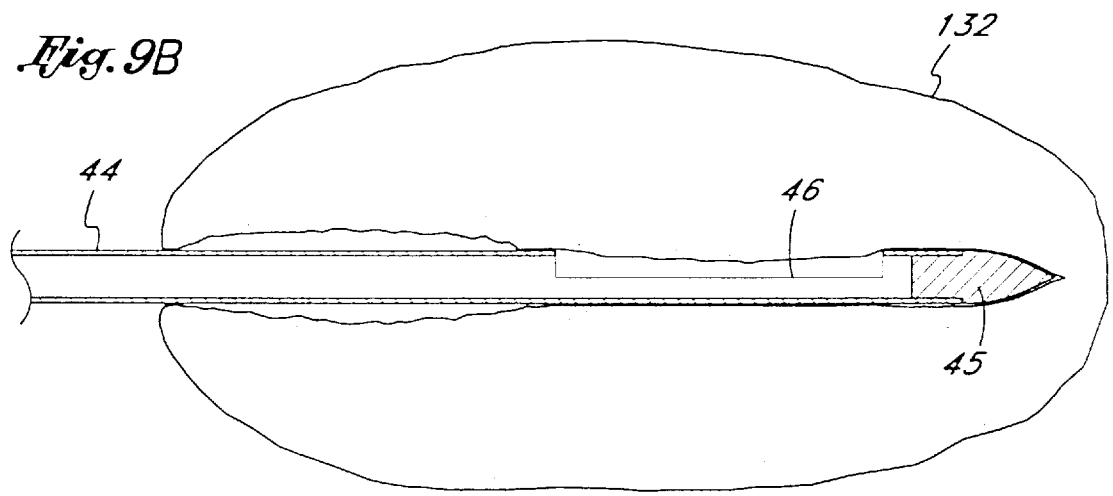
Fig. 9B
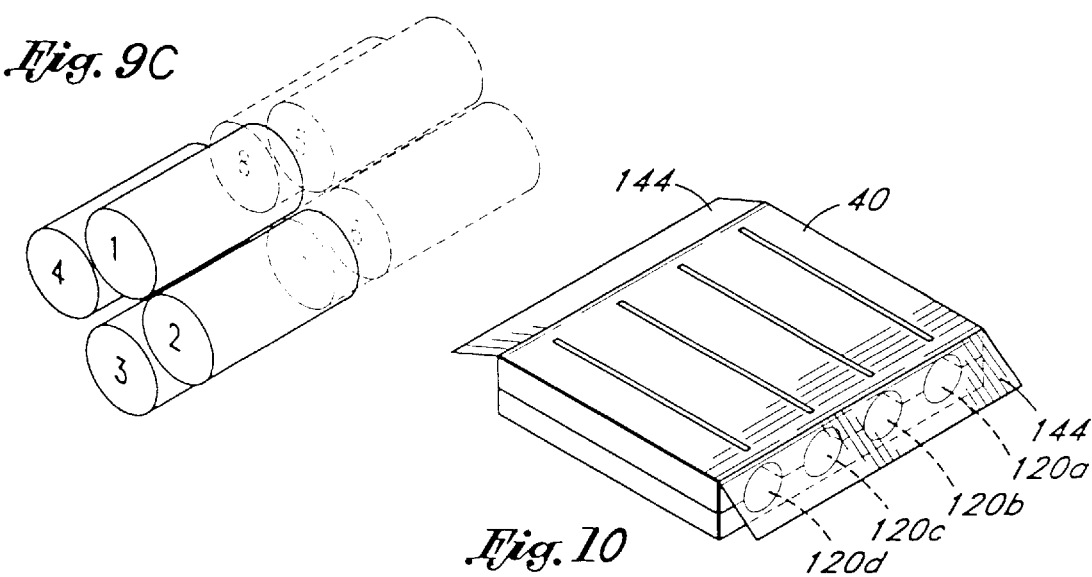
Fig. 9C
Fig. 10

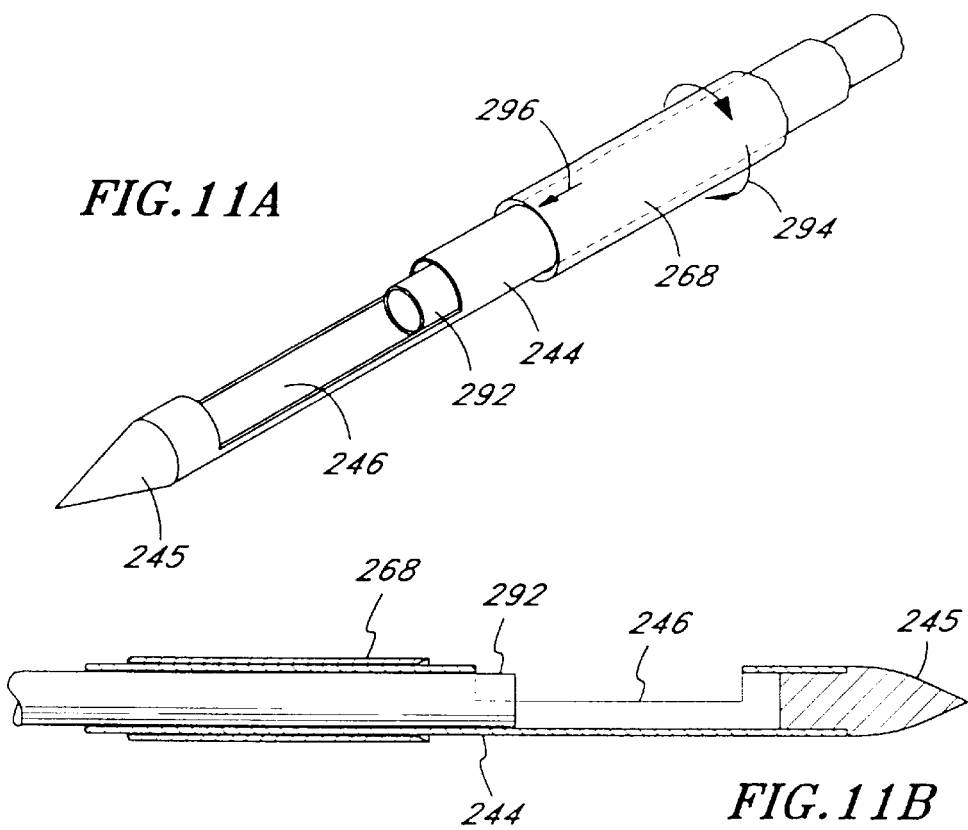
*FIG.11A*
*FIG.11B*
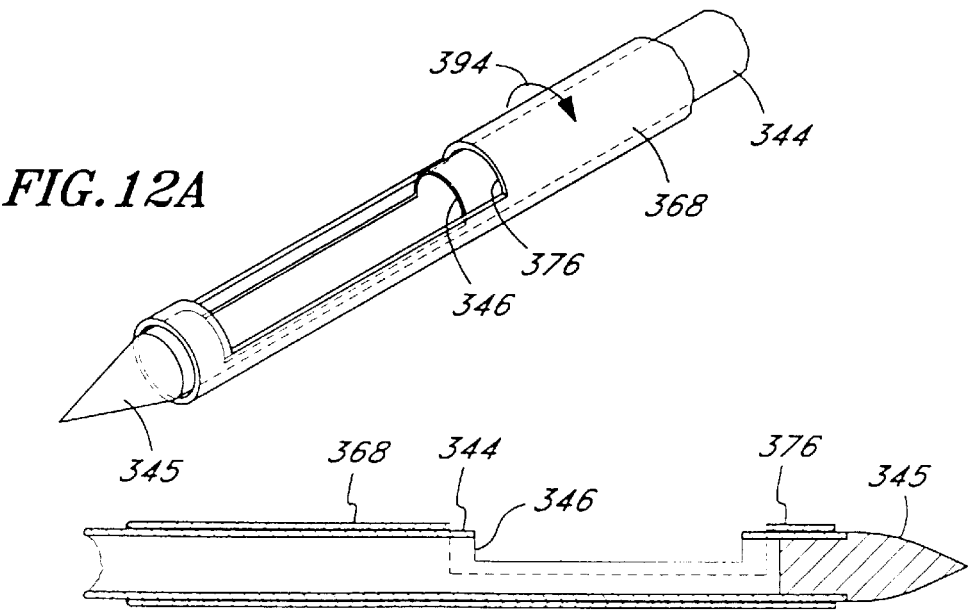
*FIG.12A*
*FIG.12B*

METHOD AND APPARATUS FOR AUTOMATED BIOPSY AND COLLECTION OF SOFT TISSUE

This application is a continuation of prior application Ser. No. 08/645,225, filed on May 13, 1996, now U.S. Pat. No. 5,775,333 which is a divisional of prior application Ser. No. 08/217,246, filed on Mar. 24, 1994, now U.S. Pat. No. 5,526,822.

FIELD OF THE INVENTION

This invention relates to biopsy instruments and methods of taking biopsies and more specifically to instruments and methods for acquiring repeated subcutaneous biopsies and for removing lesions without having to reinsert the instrument into the patient, organ, and tissue mass to be biopsied for each sample acquired.

BACKGROUND OF THE INVENTION

It is often desirable and frequently necessary to sample or test a portion of tissue from humans and other animals, particularly in the diagnosis and treatment of patients with cancerous tumors, pre-malignant conditions and other diseases or disorders. Typically, in the case of cancer, when the physician establishes by means of procedures such as palpation, x-ray or ultra sound imaging that suspicious circumstances exist, a biopsy is performed to determine whether the cells are cancerous. Biopsy may be done by an open or percutaneous technique. Open biopsy removes the entire mass (excisional biopsy) or a part of the mass (incisional biopsy). Percutaneous biopsy on the other hand is usually done with a needle-like instrument and may be either a fine needle aspiration (FNA) or a core biopsy. In FNA biopsy, individual cells or clusters of cells are obtained for cytologic examination and may be prepared such as in a Papanicolaou smear. In core biopsy, as the term suggests, a core or fragment of tissue is obtained for histologic examination which may be done via a frozen section or paraffin section.

The type of biopsy utilized depends in large part on circumstances present with respect to the patient and no single procedure is ideal for all cases. However, core biopsy is extremely useful in a number of conditions and is being used more frequently by the medical profession.

To arrive at a definitive tissue diagnosis, intact tissue is needed from an organ or lesion within the body. In most instances, only part of the organ or lesion need be sampled. However, the portions of tissue obtained must be representative of the organ or lesion as a whole. In the past, to obtain tissue from organs or lesions within the body, surgery had to be performed to locate, identify and remove the tissue. With the advent of medical imaging equipment (x-rays and fluoroscopy; computed tomography, ultrasound, nuclear medicine, and magnetic resonance imaging) it became possible to identify small abnormalities even deep within the body. However, definitive tissue characterization still requires obtaining adequate tissue samples to characterize the histology of the organ or lesion.

For example, mammography can identify non-palpable (not perceptible by touch) breast abnormalities earlier than they can be diagnosed by physical examination. Most non-palpable breast abnormalities are benign; some of them are malignant. When breast cancer is diagnosed before it becomes palpable, breast cancer mortality can be reduced. However, it is often difficult to determine if pre-palpable breast abnormalities are malignant, as some benign lesions have mammographic features which mimic malignant lesions and some malignant lesions have mammographic features which mimic benign lesions. Thus, mammography has its limitations. To reach a definitive diagnosis, tissue from within the breast must be removed and examined under a microscope. Prior to the late 1980's, reaching a definitive tissue diagnosis for non-palpable breast disease required a mammographically guided localization, either with a wire device, visible dye, or carbon particles, followed by an open, surgical biopsy utilizing one of these guidance methods to lead the surgeon to the non-palpable lesion within the breast.

The open method is illustrated in FIGS. 1A through 1E. FIG. 1A depicts an accurately localized lesion. A lesion 5 is located per one of the aforementioned visualization means. The breast 1 is pierced with a localization wire 3 with the intention of positioning the large diameter section of the wire through the center of the lesion to act as a temporary marker. In a subsequent procedure, tissue is removed around the area marked by the localization wire. The tissue is then prepared and sectioned for evaluation. Open surgical breast biopsies have many drawbacks. They can be disfiguring, expensive (in terms of direct costs to the patient and indirect costs to society from the patient being away from work), and are imperfect (the error rate for surgical biopsy has been reported to be from 2%; to 22%). FIG. 1B illustrates a localization wire 3 incorrectly placed by a radiologist. FIG. 1C illustrates a properly placed localization wire 3 but poor tissue selection 7 by the surgeon in which the lesion 5 was not harvested. FIGS. 1D and 1E illustrate a properly harvested lesion 9 with the wrong section prepared for analysis. As shown, the lesion 5 is included in the harvested tissue sample 9. However, in sectioning the tissue sample 9 along A—A and B—B for examination, the lesion 5 was missed. Any of these errors will lead to an incorrect diagnosis of the lesion. Open surgical biopsies also carry a small mortality risk (the risk of anesthesia) and a moderate morbidity rate (including bleeding, infection, and fracture or migration of the localizing wire). In cases where multiple lesions are present in the breast, a surgeon is reluctant to biopsy each lesion due to the large tissue mass that must be extracted with each lesion. The most convenient lesion is taken which results in an incomplete diagnosis. Finally, surgical breast biopsies are extremely common. In the United States, alone, it is estimated that open, surgical breast biopsies are performed on over 500,000 women annually. A-less invasive alternative has long been sought.

In the fall of 1988, two different stereotactic guidance systems were modified to allow the guiding portion of each system to accommodate spring powered devices such as the Biopty® (Bard Radiology) gun. In the summer of 1989, free-hand ultrasound guidance techniques were developed to guide the Biopty® gun to breast lesions seen by ultrasound. With the introduction of stereotactic and ultrasound guided percutaneous breast biopsies, an alternative to open, surgical breast biopsy was at hand.

With image guided percutaneous core breast biopsy, it may be possible to greatly reduce the number of open, surgical breast biopsies performed. However, there are limiting factors with image guided breast biopsies. The current generation of biopsy guns acquire specimens slowly. The placement of the needle of the gun has to be made very accurately because only one small core is obtained per insertion at any one location. To sample a lesion thoroughly, many separate insertions must be made. Finally, there is no means to completely excise a small lesion at the time of the initial diagnostic biopsy.

Stereotactic and ultrasound guidance systems have improved continuously since their introduction. Guidance systems are now more accurate, user friendly, and rapid than when they were introduced. On the other hand, automated biopsy gun systems have not evolved much since their initial introduction.

Many biopsy procedures now require a plurality of samples to be taken. For example, up to six or more samples of tissue are often required when testing the tissues of the breast, prostate gland and other body organs. In order to take multiple tissue samples using the prior art biopsy devices, each time a sample is taken, the device must be removed, and a new puncturing of the breast or organ made. This action is tedious and time consuming. Moreover, multiple manual penetrations of the organ are typically somewhat painful, and such penetrations are subject to bleeding and infection.

Multiple samples may be obtained with a device disclosed in U.S. Pat. No. 4,976,269 (Mehl). The Mehl device allows the cannula to remain in the body, but the stylette with its tissue receiving notch must be manually withdrawn from the tissue, organ, and cannula so that the test sample can be removed, a tedious and time consuming process. Samples may be compromised through prolonged sliding contact with the inside surface of the cannula during withdrawal of the stylet. To obtain a second tissue sample, the stylet is manually reinserted into the biopsy device, through the cannula, and into the organ and tissue to be sampled.

Another significant drawback of the prior art is that the stylets bearing the tissue samples must be manually handled. This exposes those persons handling the stylets to danger of infection, e.g., HIV infection. Additionally, with present devices, the stylets and samples are handled on an individual basis. The tissue samples are often damaged or destroyed due to improper handling. There is also the possibility of loss or mislabeling of the samples.

A need thus exists for a biopsy device which can take a plurality of tissue samples painlessly, in rapid sequence, minimizing handling in a way that protects the handling personnel and the tissue samples.

The True Cut® needle (Travenol Laboratories) optimally allows a roughly cylindrical shaped sample of tissue, termed a "core," to be obtained from a pointed, side cutting device, percutaneously. The True Cut® needle as shown in FIG. 1F, comprises a pointed inner stylette 11 with a side facing notch 13 to receive tissue near its pointed end (tissue receiving notch) and an outer, sharpened sliding cannula 15. The operational sequence of the True Cut® needle biopsy system is shown schematically in FIG. 1G. Once the lesion is targeted, the inner stylette 11 is thrust into the organ or lesion of interest. Tissue passively prolapses into the side facing notch 13 and the outer cannula 15 is rapidly advanced, thereby cutting off the sample of tissue contained within the notch. The entire needle system is withdrawn out of the body and the sample is manually extracted from the receiving notch 13 and handled for processing. Each specimen requires reassembly of the needle system, relocation of the lesion, and repositioning of the device.

The True Cut® needle works within a certain set a operating parameters, but is rough on organs and lesions, often only obtaining small fragments of tissue, and is quite operator dependent—some individuals are good at operating the device and some are not. FIG. 1H shows tissue 17 optimally prolapsed into the receiving chamber 13. FIG. 1I and 1J illustrate other common occurrences when using the True Cut® needle system. In FIG. 1I, tissue 17 is partially prolapsed into the receiving notch 13. Partial prolapse results in insufficient sampling, and may be caused by insufficient dwell time before cutting, by a natural bias of the tissue to migrate away from the receiving notch when it is pierced, or by forced migration of the tissue during forward movement of the cutter 15. FIG. 1J illustrates bleeding at a preceding biopsy site that has formed into a clot 19. Tissue 17 is not allowed into the tissue receiving notch 13 which is occupied by clot 19. In this situation a clot sample is obtained instead of lesion or normal tissue.

A variety of biopsy needles and guns have been described and used for obtaining tissue specimens. These guns are an improvement over manual use of the True Cut® needle. One such biopsy gun currently used is described in U.S. Pat. No. Re. 34,056, entitled "TISSUE SAMPLING DEVICE", issued to Lindgren et al. Additional examples of biopsy gun devices are disclosed in U.S. Pat. Nos. 4,600,014 and 4,958,625. The Lindgren Automatic Core Biopsy Device (ACBD) is an instrument which propels a needle set with considerable force and speed in order to pierce the tumor mass and collect the tissue sample. The ACBD has allowed physicians to accurately test tissue masses in the early stages of growth and has contributed to the medical trend of early diagnosis and successful treatment of cancer. The ACBD allows a biopsy to be performed on tumor masses as small as two millimeters in diameter. This procedure is performed under ultrasound or X-ray guidance. Tumors of this size cannot be biopsied reliably by hand since the tumor is about the same size as the biopsy needle. Manual attempts at biopsy pushes the tumor away without piercing the mass. Automatic puncture devices accelerate the needle at such a velocity that even a small tumor can be pierced. Typically, Automatic Core Biopsy Devices use the True Cut® needle set design. The stylet is advanced into the tissue under spring power followed by the cannula which cuts and traps the tissue sample in the notch of the stylet as previously discussed. The True Cut® needle yields a core sample which is semi-circular in cross-section with a length determined by the stroke of the ACBD. The most common True Cut® needle size used by ACED's is 14 gauge. The use of 14 gauge needles is a compromise between the physician's desire to use the smallest, least invasive, needle gage and the pathologist's needs for as large a tissue sample as possible to minimize false-positive and false-negative diagnosis. This compromise in needle size leads the physician to obtain multiple core samples from the biopsy site to allow the pathologist sufficient tissue for an accurate diagnosis.

The Automatic Core Biopsy Devices are able to obtain tissue from within the body with less trauma, more consistently, and in larger quantities than the manually operated True Cut® needle. However, they do have disadvantages. For example, they are typically spring powered devices and must be manually cocked with a plunger bar. Such "cocking" of the gun requires considerable force and the gun must be cocked for each biopsy cut. When actuated, the springs provided in the gun accelerate the needles until a mechanical stop position is reached creating a loud snapping noise and jerking motion which is a problem both to the physician and the patient.

Further short comings of the ACBD's include: 1) Absence of a mechanism for capturing tissue in the tissue receiving notch under varying types of tissue consistency (from soft to hard) prior to the action of the outer cutting cannula. 2) No means is provided for systematic change in position of the tissue receptacle about the long axis of the needle system. If the ACBD is held in the same orientation or is mounted in a holder, the cutting action is always in the same place, i.e., the True Cuts type needle only cuts from a 7:00 o'clock position to a 5:00 o'clock position each time it is operated.

3) They do not provide a means for systematic change in the position of the tissue receiving notch along the long axis of the stylette. 4) They do not provide for a means to allow the removal of a volume of tissue about the long axis of the needle that is larger than the diameter of the True Cut® type needle. 5) They do not provide for a means to remove a volume of tissue along the long axis of the needle that is larger in volume than the tissue receptacle of the True Cut® type needle. 6) They do not provide for a means to remove more than one core of tissue per entry into the body, organ, and lesion. With existing technology, each entry retrieves only one core sample. To obtain another core, another entry into the lesion is required. Consequently, the process of obtaining sufficient tissue to characterize heterogeneous tissue is very time consuming and tedious. With the passage of time, patient fatigue leads to patient motion and accuracy can fall. 7) They do not provide for a means to code or decode where, within the organ or lesion, the core samples originated to allow later reconstruction of the histology of the entire volume sampled. 8) They do not provide a means which allows complete removal of small lesions. Various attempts to overcome one or more of the disadvantages of the ACBD have been made.

U.S. Pat. No. 5,183,052, entitled "AUTOMATIC BIOPSY INSTRUMENT WITH CUTTING CANNULA", issued to Terwilliger describes a biopsy instrument having a stylet and a cannula wherein the instrument urges the cannula past the stylet in order to collect a tissue sample and simultaneously causes a vacuum to be communicated to the cannula in order to assist the collection of the tissue sample by the cannula.

U.S. Pat. No. 5,183,054, entitled "ACTUATED BIOPSY CUTTING NEEDLE WITH REMOVABLE STYLET", issued to Burkholder et al., discloses a biopsy device having a tubular cannula through which a stylet having a stylet cavity near the distal end is placed. The stylet is removable from the cannula and removed from the biopsy device through the housing so that the tissue sample obtained by the biopsy device may be manually retrieved while the cannula remains in place within the patient, near the area being sampled. Thereafter, the stylet may be reinserted through the housing and cannula into the patient's tissue where additional tissue samples may be obtained. In this way, trauma to the tissue that ordinarily occurs upon reinsertion of the cannula and stylet is minimized.

U.S. Pat. No. 5,234,000, entitled "AUTOMATIC BIOPSY DEVICE HOUSING A PLURALITY OF STYLETS", issued to Hakky et al. describes a biopsy device for taking a plurality of samples of tissue from a living being. The device comprises a housing having a portion arranged to be held by a person using the device, a cannula having a proximal portion and a distal portion and being coupled to the housing. A plurality of stylets are located in the housing, with each of the stylets having a proximal end, a distal end, and a tissue receiving notch located adjacent the distal end. Each stylet is individually propelled through the cannula into the body so that a portion of the tissue prolapses into the notch. The Burkholder et al. and Hakky et al. devices share all of the disadvantages of True Cut® type devices described previously with the exception of being limited to acquiring a single sample. In addition, transportation of samples by withdrawing stylettes from the instrument may compromise quality of the specimens through prolonged contact with the inside surface of the cannula.

U.S. Pat. No. 5,195,533, entitled "BIOPSY NEEDLE INSTRUMENT FOR STORING MULTIPLE SPECIMENS", issued to Chin et al. describes a biopsy needle instrument which includes a housing, an axially elongated stylet extending from the housing and a cannula coaxially extending from the housing and disposed about the stylet means. The stylet and cannula can move relative to each other and to the housing between extended and retracted positions. The stylet and cannula define, during a given operation, a specimen of a predetermined specimen axial length. The stylet includes means coacting with the cannula for storing multiple, sequentially obtained specimens within the instrument. While multiple samples may be acquired with this device, there is no provision for separating the samples from each other or maintaining the integrity of the individual samples. In addition, the volume of tissue collected per entry into the body cannot exceed the capacity of the receiving notch.

U.S. Pat. No. 4,651,753, entitled "ENDOSCOPIC MULTIPLE BIOPSY INSTRUMENT", issued to Lifton describes a biopsy instrument for use with an endoscope which includes a rigid cylindrical end attached to the distal end of a flexible arrangement of tubes. The rigid end comprises a cylindrical body having a cavity therein. The cavity extends towards the distal end of the body and is of size sufficient to hold plural samples therein. Inside the cylindrical body is a passageway which serves as a conduit for aspiration of tissue into the cavity and cylindrical body and a knife for cutting the tissue. Furthermore, a plunger is arranged coaxially with the knife for pushing individual biopsy samples of a plurality into the distal end cavity of the cylindrical body. This device is clearly for endoscopic use and would be inappropriate for use in obtaining samples from a breast or organ interior. Although this device employs an active means to urge tissue into the receiving notch, it bears the same deficiencies as the Chin device. The volume of tissue collected per bodily insertion cannot exceed the collection chamber volume, the origin of the samples cannot be differentiated, and the samples recovered must be manually handled for preparation.

The requirements of the physician and the pathologist dictate the need for an alternative approach in the function and design of the conventional ACBD, needle sets and other biopsy devices. The ideal product would allow for collection of larger tissue volume through a small opening, reliable active tissue capture mechanism, more accurate control of the location from which samples are acquired, ability to acquire multiple samples from the biopsy site without having to reinsert the biopsy needle, less traumatic transportation and storage of samples with minimum handling, and correlation of sample storage to harvest site.

SUMMARY OF THE INVENTION

Based on the prior art instruments for biopsy sampling of tissue masses and the actual present state of this art, there exists a need for an instrument which is capable of obtaining multiple samples at the biopsy site without having to insert the sampling device into the patient and organ multiple times. Additionally, there is a need to record the location from which each sample was acquired.

The present invention has means to capture tissue prior to cutting the tissue, means to direct and position the cutting chamber in arbitrary positions about and along the long axes of the invention, means for rapid and a traumatic removal of an arbitrary number of core samples with only one insertion into the body and organ, and means for coding and decoding the location from which the samples were obtained. Together, these means allow for more complete sampling of large lesions and for the complete removal of small lesions.

That portion of the present invention that is within the body can. A) pierce the lesion that is to be biopsied; B) orient and record the location of the tissue receptacle within the biopsy invention and within the body, to provide controlled sampling along and about the long axis of the invention; C) urge tissue into the tissue receptacle of the invention and retain the captured tissue therein; D) cut the captured tissue, creating a core, from the surrounding tissue; E) transport the core out of the body while maintaining the position of the biopsy invention within the body and organ; and F) repeat steps "B" through "E" any number of times (to obtain complete sampling or complete lesion removal) or can be withdrawn from the body when steps "B" through "E" have been completed.

It is the general purpose of the current invention to use medical image guidance (mammography, ultrasound, computed tomography, or magnetic resonance imaging) to position the device at or adjacent to an abnormality within the breast to allow sampling or removal of the abnormality in such a manner that the integrity of the removed tissue is preserved for histologic analysis and in such a manner that the location of the removed tissue can be determined by the sequence in which the tissue was removed. The current device is an improvement over the prior art which performs percutaneous biopsies with an automated device such as the Biopty® gun (Bard Radiology, Covington, Ga.). Use of the Biopty® gun as illustrated schematically in FIG. 1G, requires that the user remove the gun and its attached needle from the body to acquire and remove one core sample. Furthermore, each sample must be manually handled for preparation. Consequently, the volume of tissue that can be acquired is limited by the time consuming nature of the current generation of automated biopsy guns. The present invention allows many samples to be acquired and removed with one insertion of the device into the body and allows the acquisition and removal to occur rapidly with minimum handling. With this type of automation, sampling and/or complete removal of the abnormality is possible.

In a first primary embodiment, the present invention is a biopsy device for acquiring a plurality of sequentially biopsied, discrete samples of tissue comprising: a rotatable retaining fixture; an elongate outer piercing needle having a sharpened distal end for piercing tissue, the elongate outer piercing needle attached to the rotatable retaining fixture such that the sharpened distal end is held in a fixed position within the tissue mass at a predetermined target position, wherein the elongate outer piercing needle has a lateral opening located proximal to the sharpened distal end for receiving a portion of the tissue mass which is positioned adjacent to the lateral opening; an elongate inner cannula disposed coaxially and slidably within the elongate outer piercing needle, the elongate inner cannula having a sharpened distal end for cutting the portion of tissue protruding into the elongate outer piercing needle lateral opening when the elongate inner cannula slides past the lateral opening thereby depositing the portion of cut tissue within the elongate inner cannula proximal to the sharpened distal end; an inner cannula driver connected to the elongate inner cannula and configured to move the elongate inner cannula axially within the elongate outer cannula; and a tissue sample cartridge having a plurality of tissue sample receptacles, the tissue sample cartridge located proximal to a distal end of the elongate outer cannula and configured to receive the portion of cut tissue which is in the elongate inner cannula proximal to the sharpened distal end when the inner cannula driver withdraws the inner cannula from the outer cannula. This embodiment may further comprise an elongate knock out pin disposed coaxially and slidably within the elongate inner cannula, the elongate knock out pin having a closed distal end with a vent hole therein. Additionally, the a vacuum source may be attached to a proximal end of the elongate knock out pin.

In a second primary embodiment, the invention is a biopsy instrument comprising: a first hollow tubular member having a longitudinal axis, a proximal portion, a distal portion, a tissue receiving port positioned laterally a selected distance from the distal portion, and a tissue discharge port positioned a selected distance from the proximal portion; and a tissue sample cassette having a plurality of tissue sample compartments, wherein each of the tissue sample compartments has a tissue receiving port, the tissue sample cassette having a plurality of positions with respect to the first hollow tubular member tissue discharge port such that each of the tissue sample compartment receiving ports may be sequentially aligned with the first hollow tubular member discharge port. This embodiment may further comprise a body having a portion arranged to be mounted to a stereotactic guidance unit; and a rotary drive mechanism mounted to the body and to the proximal portion of the first hollow tubular member. Alternatively, this embodiment may further comprises a first hollow tubular member rotatable retaining fixture coupled to the proximal portion of the first hollow tubular member, wherein rotation of the fixture controls the angular orientation of the laterally disposed tissue receiving port. In yet another alternative embodiment, the first hollow tubular member further comprises a vacuum manifold positioned proximal to the laterally disposed tissue receiving port. Another alternative embodiment further comprises: a second hollow tubular member having: a longitudinal axis, a proximal portion, a distal portion, a tissue cutting portion positioned a selected distance from the distal portion, wherein the second hollow tubular member is positioned coaxially with the first hollow tubular member, the first hollow tubular member tissue receiving port and the second hollow tubular member tissue cutting portion coacting to sever tissue extending through the tissue receiving port. This alternate embodiment may further comprise a second hollow tubular member driving system coupled to the proximal portion of the second hollow tubular member, wherein the second hollow tubular member driving system controls the rotational motion of the second hollow tubular member about the longitudinal axis and the linear motion of the second hollow tubular member along the longitudinal axis. In this embodiment, the second hollow tubular member driving system may further comprise an ultrasonic driver. This alternate embodiment may further comprise an elongate knock out pin disposed coaxially and slidably within the second hollow tubular member, the elongate knock out pin having a closed distal end with a vent hole therein. The elongate knock out pin may further have a vacuum source attached to a proximal end thereof.

In a third primary embodiment, the invention is for a biopsy method comprising the steps of: introducing a hollow tubular member having a laterally disposed tissue receiving port located a preselected distance from a distal portion and a tissue discharge port located at a preselected distance from a proximal portion into a tissue mass to be sampled; severing a tissue sample from the tissue mass which has entered the tissue receiving port; transporting the severed tissue sample through the hollow tubular member to the proximal portion of the hollow tubular member; and depositing the severed tissue sample in one of a plurality of tissue sample compartments in a sample cassette. The method may further comprise the step of rotating the laterally disposed tissue receiving port of the hollow tubular member to a predetermined angular orientation. Alternatively, the method may further comprise the step of applying a vacuum to the laterally disposed tissue receiving port of the hollow tubular member. Additionally, the step of applying a vacuum may further comprise the step of distributing the vacuum uniformly over an area defining the laterally disposed tissue receiving port of the hollow tubular member. The method may further comprise the step of maintaining a record of the location in the tissue mass from which each tissue sample is acquired. In some embodiments, the method further comprises the step of processing the tissue samples for examination without removing them from the tissue sample compartments in the sample cassette.

In a fourth primary embodiment, the invention is a biopsy instrument comprising: a hollow piercing needle having a laterally disposed tissue receiving port at a distal end and a sample discharge port at a proximate end, wherein the hollow piercing needle is mounted on a rotatable positioner for controlling the angular orientation of the tissue receiving port; and a sample cassette having a plurality of compartments coupled to the sample discharge port, wherein each of the plurality of compartments is correlated with a specific angular orientation of the tissue receiving port.

In a fifth primary embodiment, the invention is a biopsy instrument for extracting intact tissue samples from within a body comprising: (a) an elongated primary hollow tube with a closed distal end; (b) a lateral tissue receiving port near the distal end of the elongated primary hollow tube, wherein the lateral tissue receiving port is configured for positioning within the body; (c) a proximal tissue discharge port near a proximal end of the elongated primary hollow tube, wherein the proximal tissue discharge port is configured for positioning outside the body; and (d) a tissue specimen cassette containing multiple receptacles configured to receive tissue specimens mated to the proximal tissue discharge port. A first alternate embodiment of the fifth primary embodiment may further comprise: (a) an inner hollow tube movably positioned within the elongated primary hollow tube, the inner hollow tube having a sharpened distal end; and (b) an inner hollow tube driver attached to a proximal end of the inner hollow tube, the inner hollow tube driver configured: 1) to move the inner hollow tube past the lateral tissue receiving port thereby cutting off a tissue specimen and thereby positioning the tissue specimen within the inner hollow tube, and 2) to move the inner hollow tube to the proximal tissue discharge port. In some configurations, the inner hollow tube driver is further configured to rotate the sharpened distal end of the inner hollow tube to facilitate cutting or alternatively to oscillate the sharpened distal end of the inner hollow tube to facilitate cutting. Additionally, the first alternate embodiment may further comprise a packing plug located within the distal end of the elongated primary hollow tube; the packing plug shaped to mate with the inside of the distal end of the inner hollow tube to pack the tissue specimen within the inner hollow tube. A second alternate embodiment of the fifth primary embodiment further comprises: (a) an outer hollow tube movably positioned outside the elongated primary hollow tube with a closed distal end, the outer hollow tube having a sharpened distal end; (b) an outer hollow tube driver attached to a proximal end of the outer hollow tube, the outer hollow tube driver configured to move the outer hollow tube past the lateral tissue receiving port at the distal end of the elongated primary hollow tube thereby cutting off a tissue specimen and depositing the tissue specimen within the elongated primary hollow tube; and (c) a driver attached to the proximal end of the elongated primary hollow tube configured to move the elongated primary hollow tube with a closed distal end to the proximal tissue discharge port. In this embodiment, the outer hollow tube driver may be further configured to rotate the sharpened distal end of the outer hollow tube to facilitate cutting or alternatively to oscillate the sharpened distal end of the outer hollow tube to facilitate cutting. A third alternate embodiment of the fifth primary embodiment further comprises an elongate knock out pin disposed coaxially and slidably within the elongated primary hollow tube, the elongate knock out pin having a closed distal end with a vent hole therein. This alternate embodiment may also include a vacuum source attached to a proximal end of the elongate knock out pin. A fourth alternate embodiment of the fifth primary embodiment further comprises a registration mechanism to correlate the orientation of the lateral tissue receiving port with a unique tissue sample cassette sequence number to allow reconstruction of the spatial distribution of the collected tissue specimens. A fifth alternate embodiment of the fifth primary embodiment further comprises a vacuum chamber connected to the lateral tissue receiving port to actively pull tissue into the lateral tissue receiving port in the elongated primary hollow tube. A sixth alternate embodiment of the fifth primary embodiment further comprises a proximal longitudinal depth controlling mechanism connected to the elongated primary hollow tube configured to translate the outer hollow tube to selected depths along the elongate hollow tube's long axis whereby the biopsy instrument can extract multiple intact tissue samples longitudinally from within a target lesion or organ while, at all times, maintaining the instrument within the target. In a seventh alternate embodiment of the fifth primary embodiment, the invention further comprises a proximal rotational drive controlling mechanism connected to the elongated primary hollow tube configured to rotate the elongate hollow tube to selected positions about the elongate hollow tube's long axis whereby the biopsy instrument can extract multiple intact tissue samples radially from within a target lesion or organ while, at all times, maintaining the instrument within the target. In an eighth alternate embodiment of the fifth primary embodiment, the invention further comprises: (a) a pointed distal end on the elongated primary hollow tube with a closed distal end; and (b) a proximal piercing mechanism connected to the elongated primary hollow tube with a closed distal end, the proximal piercing mechanism configured to translate the elongated hollow tube to selected depths along the elongated hollow tube's long axis whereby the biopsy instrument can pierce a target lesion from without the lesion. A ninth alternate embodiment of the fifth primary embodiment further comprises a guidance system for positioning the elongated primary hollow tube which is selected from the group including, endoscopy, computed tomography, ultrasound, fluoroscopy, stereotaxis, and magnetic resonance imaging.

A sixth primary embodiment of the present invention is a biopsy instrument comprising: (a) an elongated primary hollow tube with a closed distal end; (b) a lateral tissue receiving port near the distal end of the elongated primary hollow tube, wherein the lateral tissue receiving port is configured to receive tissue; (c) a vacuum chamber attached to the distal end of the elongated primary hollow tube; and (d) a plurality of communicating holes between the distal end of the elongated primary hollow tube and the vacuum chamber to pull tissue into the elongated primary hollow tube.

A seventh primary embodiment of the present invention is biopsy method for excavating a large volume of tissue from within a body by repetitively removing smaller tissue specimens through a small opening in the body, the small opening just large enough to withdraw one tissue specimen, the method comprising the steps of: (a) introducing an elongated primary hollow tube with a closed distal end into the body, wherein the elongated primary hollow tube has a lateral tissue receiving port near its distal end and a proximal tissue discharge port with the proximal tissue discharge port mated to a tissue specimen cassette containing a plurality of specimen compartments; (b) positioning the lateral tissue receiving port within the body near a target lesion or organ; (c) positioning the proximal tissue discharge port outside the body; (d) cutting a tissue specimen which has entered the tissue receiving port; (e) transporting the cut tissue specimen through the elongated primary hollow tube to the proximal tissue discharge port; and (f) depositing the cut tissue specimen into a receptacle within the tissue specimen cassette. A first alternate embodiment of the seventh primary embodiment further comprises the step of rotating the lateral tissue receiving port to a predetermined angular orientation. A second alternate embodiment of the seventh primary embodiment further comprises the step of translating the lateral tissue receiving port to a predetermined depth within the body. In a third alternate embodiment of the seventh primary embodiment, the method further comprises the step of applying a vacuum to the lateral tissue receiving port to encourage tissue capture. This embodiment may further comprise the step of distributing the vacuum uniformly over an area defining the lateral tissue receiving port. A fourth alternate embodiment of the seventh primary embodiment further comprises the step of maintaining a record of the orientation of the lateral tissue receiving port and the number of the chamber in the tissue specimen cassette to allow special correlation of the origin of each specimen. A fifth alternate embodiment of the seventh primary embodiment further comprises the step of packing the tissue specimen into a transport means with a packing plug. This embodiment may further include the step of ejecting the tissue specimen from the transport means into the tissue specimen cassette. In a sixth alternate embodiment of the seventh primary embodiment, the invention further comprises the step of piercing the target lesion by actively driving the elongated primary hollow tube from without the targeted lesion to within the lesion.

An eighth primary embodiment of the present invention is a biopsy device comprising: a housing; a tubular piercing member having a distal pointed end, and a laterally positioned tissue receiving port proximate the distal pointed end which opens into a tissue sample chamber, wherein the tubular piercing member is rotably attached to the housing and held in a fixed position within a tissue mass; a cannular cutting member coacting with the tubular piercing member to cut a first tissue sample from the tissue mass such that the first tissue sample can be transported by the second cutting member to said tissue sample receptacle.

The present invention is an improved automated biopsy system which allows better percutaneous sampling of breast lesions for diagnostic purposes and allows complete removal of small breast abnormalities or removal of other tissue for a variety of reasons percutaneously through a tiny skin incision. Although initially designed for breast biopsies, the system may also be used to biopsy other organs, for example, the prostate.

BRIEF DESCRIPTION OF THE DRAWINGS

The above noted advantages and other characteristic features of the present invention will be apparent through reference to the following detailed description of the preferred embodiments and accompanying drawings, wherein like reference numerals designate corresponding parts and wherein:

FIG. 2 shows a schematic plan view of the biopsy instrument of the present invention shown in FIG. 1K;

FIG. 3 shows individual components of the biopsy instrument shown in FIG. 1K and FIG. 2;

FIG. 4 shows a detailed view of a hollow outer piercing needle and sample cassette;

FIG. 5A shows a cross sectional view of the sample cassette housing and the tissue sample cassette;

FIGS. 6A, 6B, 6C, 6D, 6E, 6F, 6G and 6H illustrate sequential steps in the operation of the biopsy instrument of the present invention;

FIGS. 7A, 7B, 7C and 7D show cross sectional end views of the hollow outer piercing needle piercing the tissue mass in four different angular positions;

FIGS. 8A, 8B, 8C and 8D show cross sectional views of the tissue sample cassette with tissue samples deposited therein for the same four angular positions shown in FIGS. 7A, 7B, 7C and 7D, respectively;

FIGS. 9A, 9B and 9C illustrate a precision procedure for acquiring and tagging multiple tissue samples both along an axis and about the axis with a single entry into the tissue mass being sampled.

FIG. 10 shows an embodiment of a tissue sample cassette having covers over the tissue chambers;

FIGS. 11A and 11B illustrate a first alternate cutting mechanism for the biopsy instrument having a rotation/translation outer cannular cutter;

FIGS. 12A and 12B illustrate a second alternate cutting mechanism for the biopsy instrument having a rotation only outer cannular cutter;

DETAILED DESCRIPTION OF THE PREFERRED EMBODIMENTS

Figure 1A:
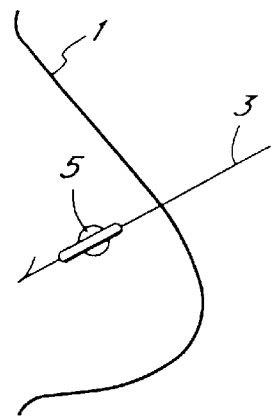
FIGS. 1A through 1E show the sequence and errors related to surgical biopsy.
Figure 1B:
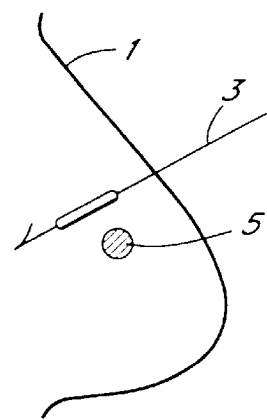
Figure 1C:
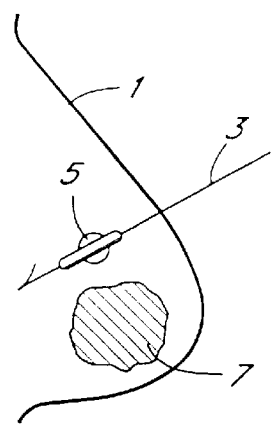
Figure 1D:
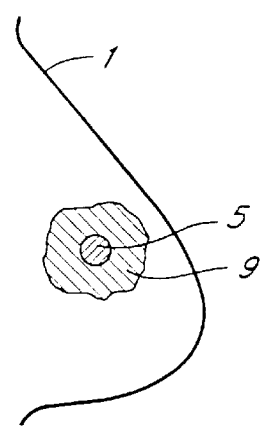
Figure 1E:
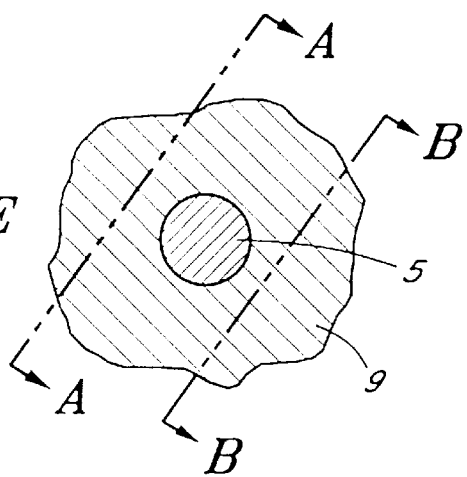
Figure 1G:
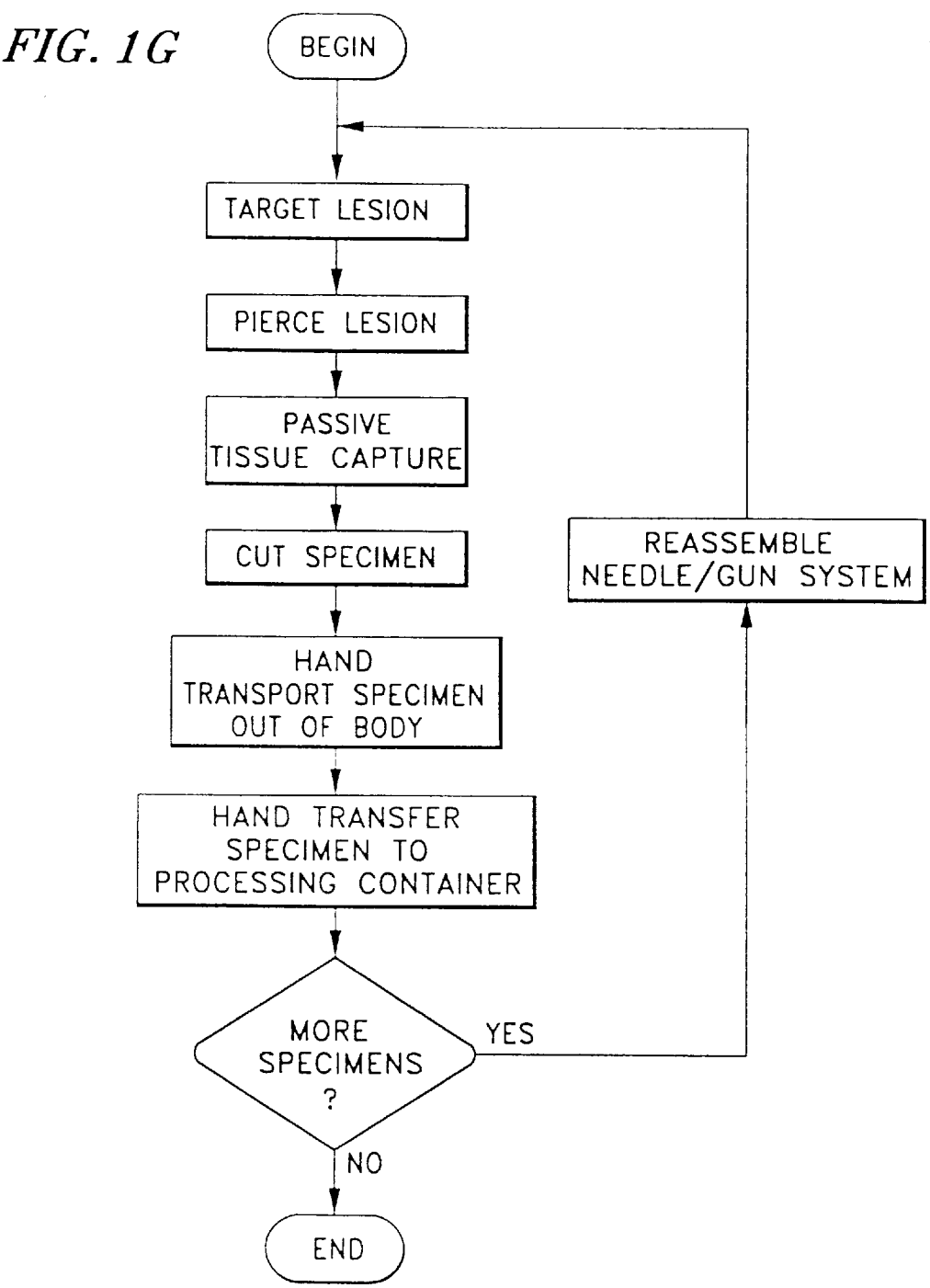
FIG. 1G shows the operational sequence of events for the True Cut® needle system.
Figure 1F:
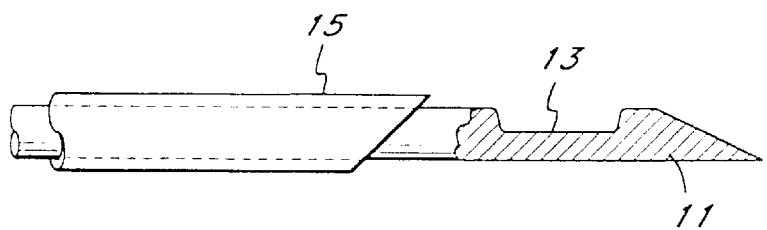
FIG. 1F shows the business end of the True Cut® needle system.
Figure 1H:
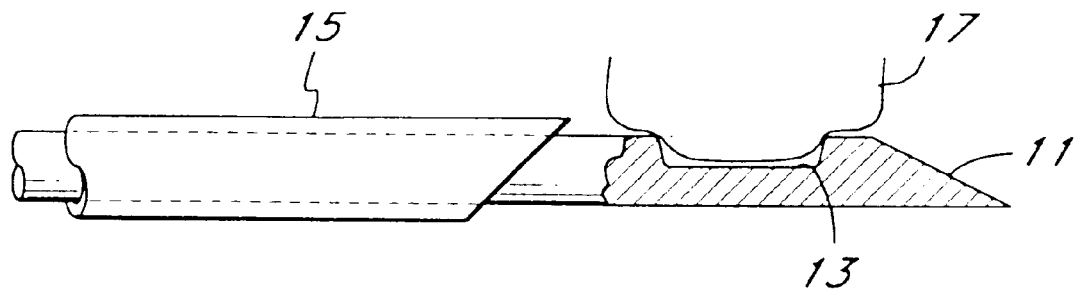
FIGS. 1H through 1J show common occurrences surrounding use of the True Cut® needle system.
Figure 1I:
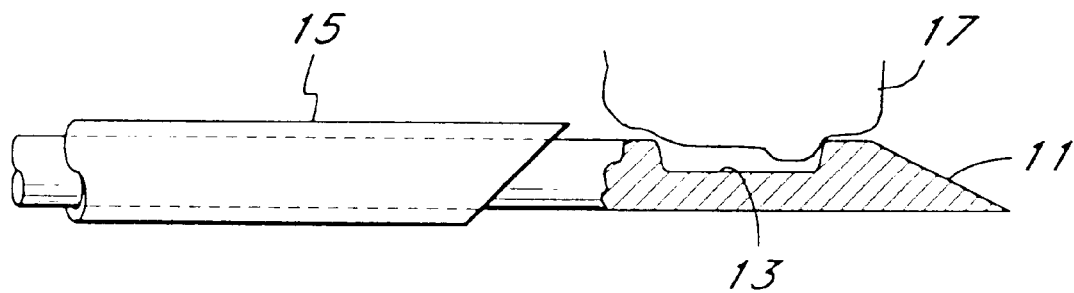
Figure 1J:
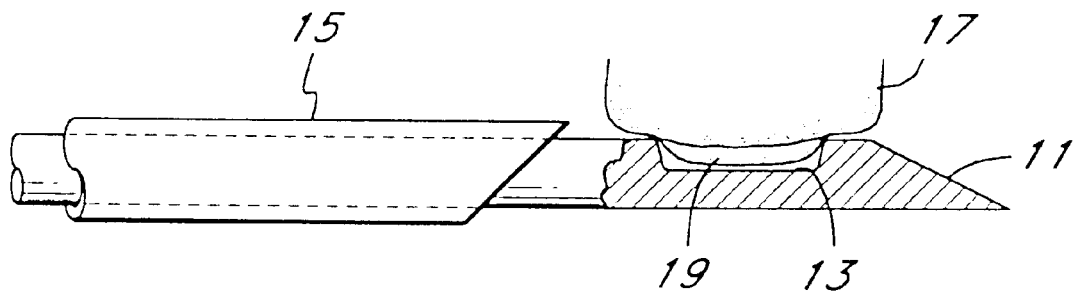
Figure 1K:
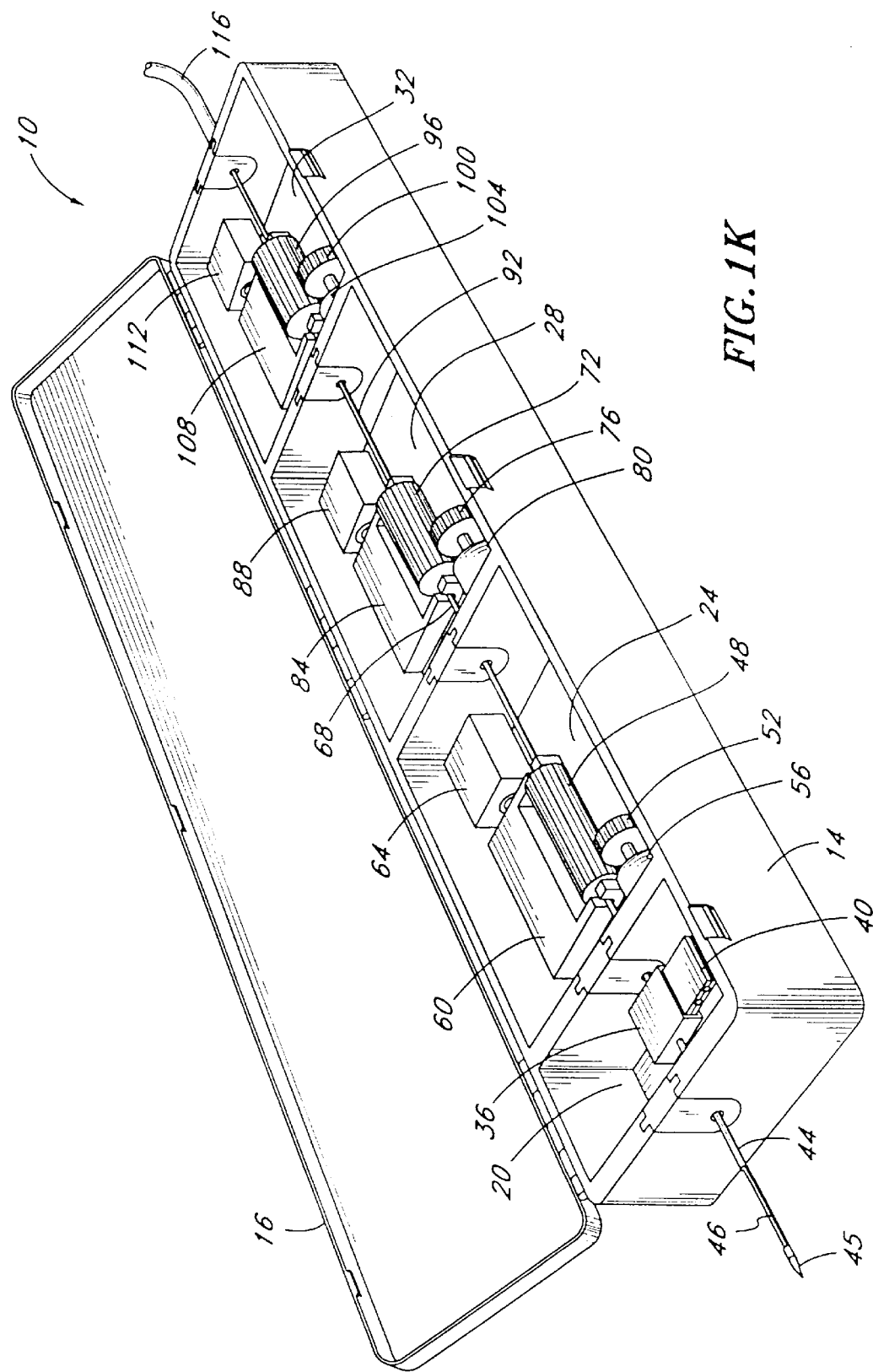
FIG. 1K shows a perspective view of a first preferred embodiment of the biopsy instrument of the present invention.

Referring to FIGS. 1K, 2, 3 and 4 wherein FIG. 1K shows a perspective view of a first preferred embodiment 10 of the biopsy instrument of the present invention, FIG. 2 shows a schematic plan view of the biopsy instrument 10, FIG. 3 shows individual components of the biopsy instrument 10, and FIG. 4 shows a detailed view of a hollow outer piercing needle and sample cassette. Biopsy instrument 10 comprises a housing 14 having a lid 16. The housing 14 is divided into four sections including a sample cassette chamber 20, an outer piercing needle driver chamber 24, an inner cutter driver chamber 28 and a knock out pin driver chamber 32. Mounted in the sample cassette chamber 20 is a cassette housing 36 which contains a tissue sample cassette 40. A hollow outer piercing needle 44 is attached to the cassette housing 36 as is an outer piercing needle elongate indexing gear 48. A distal end of the hollow outer piercing needle 44 includes a point 45. Hollow outer piercing needle 44 also includes a tissue receiving port 46. A piercing needle drive gear 52 attached to a piercing needle drive motor 56 meshes with the piercing needle indexing gear 48. Piercing needle indexing gear 48 is movably mounted within outer needle driver chamber 24 on a piercing needle sliding support 60. A piercing needle linear driver 64 is connected to the piercing needle sliding support 60.

A cannular inner cutter 68 having a cannular inner cutter elongate indexing gear 72 attached to a proximal end is movably positioned coaxially within the hollow outer piercing needle 44. A cannular inner cutter drive gear 76 attached to a cannular inner cutter drive motor 80 meshes with the cannular inner cutter elongate indexing gear 72. Cannular inner cutter elongate indexing gear 72 is movably mounted within inner cutter driver chamber 28 on an inner cutter sliding support 84. An inner cutter linear driver 88 is connected to the inner cutter sliding support 84.

A tubular knock out pin 92 having a tubular knock out pin elongate indexing gear 96 attached to a proximate end is movably positioned coaxially within the cannular inner cutter 68. A tubular knock out pin drive gear 100 attached to a tubular knock out pin drive motor 104 meshes with the tubular knock out pin elongate indexing gear 96. Tubular knock out pin elongate indexing gear 96 is movably mounted within knock out pin driver chamber 32 on a tubular knock out pin sliding support 108. A tubular knock out pin linear driver 112 is connected to the tubular knock out pin sliding support 108. A vacuum connection 116 is located at a proximal end of tubular knock out pin 92.

A control unit 118 (FIG. 2) controls the operation of drive motors 56, 80, 104; linear drivers 64, 88, 112; and a vacuum source connected to port 116. The control unit 118 may be programmed by the user to collect a set of specimens from discreet locations, and is capable of outputting a record of such locations to correlate individual samples to the discreet locations.

A cross sectional view of the sample cassette housing 36 and the tissue sample cassette 40 is shown in FIG. 5A. Tissue sample cassette 40 includes tissue containment chambers 120a, 120b, 120c and 120d. The hollow outer piercing needle 44, cannular inner cutter 68 and tubular knock out pin 92 are shown positioned in tissue containment chamber 120a. Sample cassette 40 includes indexing ridges 124 which cooperate with indexing grooves 128 formed in sample cassette housing 36 to provide precision and repeatable positioning of the sample cassette 40 within the housing 36.

Operation of the biopsy instrument is described with reference to FIGS. 6A through 6H. FIG. 6A illustrates the distal end point 45 of hollow outer piercing needle 44 in position to pierce a tissue sample 132 which is to be sampled. The initial global position of the point 45 with respect to the tissue area being sampled is determined by the overall position of biopsy instrument 10 of the present invention with respect to the patient. For example, the entire biopsy instrument 10 may be mounted on a commercially available stereotactic guidance system (e.g., Fischer), not shown, commonly used in the medical field for accurate positioning of a variety of medical devices with respect to a patient. A detailed description of such a motorized biopsy needle positioner, i.e., stereotactic guidance system, is given in U.S. Pat. No. 5,240,011, issued on Aug. 31, 1993, to Michael Assa, which is hereby incorporated herein by reference. The suspect lesion within the tissue sample 132 which is to be sampled is targeted according to the instructions provided with the stereotactic guidance system. As shown in FIG. 6A, the stereotactic guidance system has positioned the biopsy instrument 10 such that distal end point 45 is immediately adjacent a surface of the tissue sample 132 in which the lesion to be sampled is located. Furthermore, it is object of the guidance system to position the needle assembly such that the center of the lesion is centered within the tissue receiving notch immediately after firing the needle assembly. It will be understood that when the lesion to be sampled is located more deeply within the tissue sample 132, the stereotactic guidance system will advance the point 45 through the surrounding tissue surface and advance the point 45 until it is adjacent the specific lesion region to be sampled.

Once the point 45 is adjacent the specific lesion region to be sampled, fine tuning of the location of the point 45 within the tissue sample 132 is accomplished by control unit 118 which sends signals to linear actuator 64 thus advancing and retracting the hollow outer piercing needle 44 along its axis. As shown in FIG. 6B, linear actuator 64 has advanced the hollow outer piercing needle 44 into the tissue sample 132. Linear actuators 64, 88, 112 may be any of a variety of devices capable of inducing linear motion including solenoids, pneumatic cylinders, potential energy devices such as springs, motors, etc.

As shown in FIG. 6C, after the hollow outer piercing needle 44 has been positioned at the precise location within the tissue 132 at which it is desired to obtain a tissue sample, the control unit 118 actuates a vacuum source which is applied to the vacuum connection 116 of the tubular knock out pin 92 thereby generating a region of low pressure 136 within the hollow outer piercing needle 44. A vent hole 138 in the distal end of the tubular knock out pin 92 provides an air passageway between the hollow interior of the tubular knock out pin 92 and the hollow interiors of the hollow outer piercing needle 44 and the cannular inner cutter 68. The low pressure created by the vacuum source in region 136 facilitates the prolapse of tissue 132a immediately adjacent tissue receiving port 46 into the hollow interior of hollow outer piercing needle 44.

The prolapsed tissue sample 132a is severed from the main tissue mass 132 by the advancement of the cannular inner cutter 68 as shown in FIG. 6D. The advancement of cannular inner cutter 68 is activated by control unit 118 which sends signals to linear actuator 88 thus advancing the cannular inner cutter 68 along its axis within the hollow outer piercing needle 44 past the tissue receiving port 46 thereby severing prolapsed tissue sample 132a from the main tissue mass 132. After being severed from tissue mass 132, the tissue sample 132a is packed into the cannular cutter 68 as it moves forward against pin 41 and rests inside the cannular inner cutter 68. The control unit 118 then activates linear actuator 88 in the reverse direction to withdraw the cannular inner cutter 68 and the tissue sample 132a. Tissue sample 132a is held in the cannular inner cutter 68 by friction with the inner walls of the cannula and by the suction created by the vacuum source and delivered into the region of low pressure 136 by the tubular knock out pin 92. The withdrawal of the tissue sample 132a is illustrated in FIG. 6E.

Tissue sample 132a is deposited in tissue sample cassette 40 as shown in FIG. 6F. The tubular knock out pin 92 is positioned coaxially within the cannular inner cutter 68 and the hollow outer piercing needle 44 such that a distal end of the tubular knock out pin 92 is near the proximal end of the tissue containment chamber 120a. As the cannular inner cutter 68 is withdrawn through the tissue containment chamber 120a, the tissue sample 132a is stopped within the tissue containment chamber 120a by the distal end of the tubular knock out pin 92.

The final release of the tissue sample 132a from the tubular knock out pin 92 into the tissue containment chamber 120a is illustrated in FIGS. 6G and 6H. In FIG. 6G, the vacuum source has been turned off by control unit 118 thereby releasing the tissue sample 132a from the distal end of the tubular knock out pin 92. FIG. 6H shows the tubular knock out pin 92 in a withdrawn position completely clear of the tissue sample cassette 40 and tissue sample 132a resting within the tissue containment chamber 120a.

In some applications, it may be advantageous to obtain a tissue sample as shown in FIGS. 6A–6H without application of a vacuum to the tubular knock out pin 92. In other applications, it may be advantageous to apply vacuum to tissue receiving port 46 through a second dedicated lumen fully described in reference to FIG. 16.

FIGS. 7 and 8 show the cross sectional views indicated in FIG. 6H. These figures illustrate a procedure whereby four samples of tissue mass 132 are acquired from four different angular positions and deposited in sample cassette 40 without removing the hollow outer piercing needle 44 and tissue receiving port 46 from the tissue mass 132. Furthermore, the integrity of each sample is preserved and a record of the location from which each of the four samples is acquired is created by storing the samples in individual sample containment compartments 120. FIGS. 7A, 7B, 7C and 7D show cross sectional end views of the hollow outer piercing needle 44 piercing the tissue mass 132 in four different angular positions. FIGS. 8A, 8B, 8C and 8D show cross sectional views of the tissue sample cassette 40 with tissue samples deposited therein for the same four angular positions shown in FIGS. 7A, 7B, 7C and 7D, respectively.

The cross sectional end view of the hollow outer piercing needle 44 piercing the tissue mass 132 shown in FIG. 7A corresponds to the angular orientation of the hollow outer piercing needle 44 in FIGS. 6A–6H. That orientation is such that the tissue receiving port 46 of hollow outer piercing needle 44 defines an arc 140a within which surrounding tissue sample 132a can prolapse into the hollow outer piercing needle through the receiving port 46. The arc 140a is governed by the shape of receiving port 46 and spans an angular range of from approximately 10:00 o'clock to approximately 2:00 o'clock. Tissue sample 132a is severed from tissue mass 132, transported through hollow outer piercing needle 44 and deposited into sample containment chamber 120a (FIG. 8A) as previously described in reference to FIGS. 6A–6H.

Outer piercing needle drive motor 56 (FIG. 2) rotates the hollow outer piercing needle 44 about its axis 90 degrees to the angular position shown in FIG. 7B. This rotation positions the tissue receiving port 46 adjacent a new region of tissue mass 132 defined by an arc 140b. Additionally, the tissue sample cassette 40 is moved within cassette housing 36 to align the sample containment chamber 120b with the axis of hollow outer piercing needle 44. The arc 140b spans an angular range of from approximately 1:00 o'clock to approximately 5:00 o'clock. Tissue sample 132b is severed from tissue mass 132, transported through hollow outer piercing needle 44 and deposited into sample containment chamber 120b as previously described. Similarly, tissue samples 132c and 132d are acquired from angular positions 140c and 140d, respectively. The arc 140c spans an angular range of from approximately 4:00 o'clock to approximately 8:00 o'clock and arc 140d spans an angular range of from approximately 7:00 o'clock to approximately 11:00 o'clock. It will be understood that the above procedure is illustrative of the general capabilities of the present invention. Rotations about the axis are not limited to 90 degrees but may be of any number of degrees desired. Also, arcs may span more or less than the 4 hour increment described by 140a through 140d.

Figure 5B:
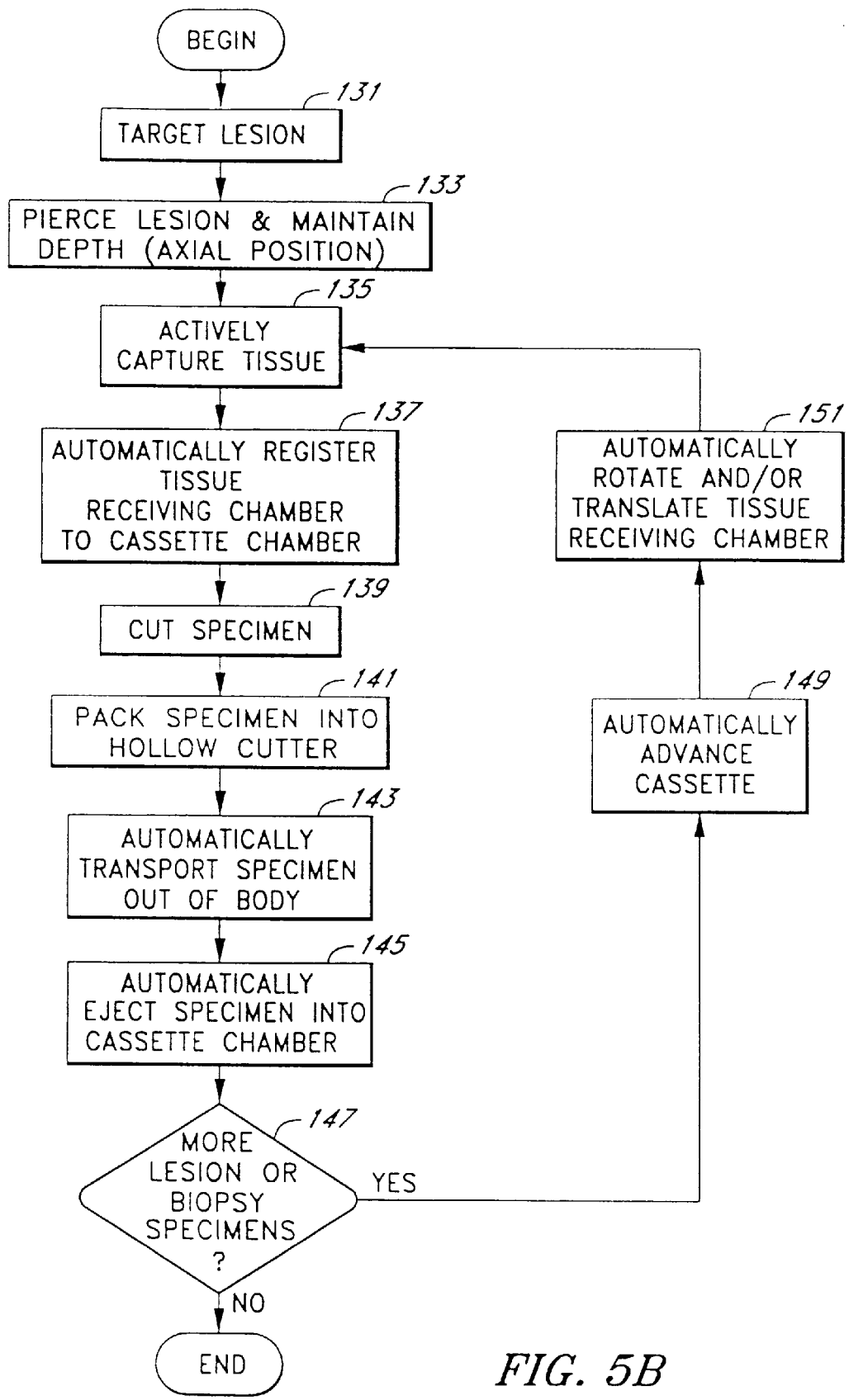
FIG. 5B shows a sequence of operating events for the present invention.

FIG. 5B is a flow chart which summarizes the operation of the invention as previously described in reference to FIGS. 6A–6H, 7A–7D and 8A–8D. The lesion to be sampled is targeted, activity block 131 (FIG. 6A), followed by piercing of the lesion and maintaining the depth or axial position, activity block 133 (FIG. 6B). The tissue is then actively captured in the tissue receiving port 46, activity block 135 (FIG. 6C). Additionally, the tissue receiving chamber 46 is automatically registered to the sample cassette chamber 120a as indicated by activity block 137. In activity blocks 139 and 141, the tissue specimen 132a is severed from tissue mass 132 and packed into the hollow cutter 66 (FIG. 6D). The severed tissue sample 132a is then transported out of the body as indicated by activity block 143 (FIG. 6E) and placed into the sample cassette chamber 120a as indicated by activity block 145 (FIGS. 6F–6H). If more lesion or biopsy samples are required, decision block 147, the process advances to activity block 149 wherein the sample cassette is advanced to a new sample chamber, then to activity block 151 wherein the tissue receiving chamber 46 is positioned for acquiring another sample (FIGS. 7 and 8). The process then repeats beginning in block 135. If no additional lesion or biopsy samples are required in decision block 147, the process is terminated.

In addition to acquiring multiple tissue samples around the axis of the hollow outer piercing needle 44 with a single entry into the tissue mass 132 as described with reference to FIGS. 6 and 7, the biopsy instrument 10 of the present invention may be used to acquire multiple tissue samples along the axis of the hollow outer piercing needle 44. This procedure is illustrated in FIGS. 9A, 9B and 9C. FIG. 9A shows the tissue receiving port 46 of the hollow outer piercing needle 44 in a first axial position wherein four samples have been removed about the axis from the first axial position as previously described in reference to FIGS. 7 and 8. FIG. 9C illustrates schematically the relative orientation of the four samples ("1", "2", "3" and "4") which have been removed from about the first axial position of the hollow outer piercing needle 44 shown in FIG. 9A. The hollow outer piercing needle 44 is then moved forward along its axis to the second axial position shown in FIG. 9B by the outer piercing needle linear driver 64 (FIG. 2). From the second axial position, four additional samples ("5", "6", "7" and "8") about the axis are removed. Using this procedure, a relatively large volume of tissue can be removed from a prespecified area within tissue mass 132 without having to remove and relocate the biopsy instrument from that prespecified area for each piece of the sample acquired. Additionally, the location from which each piece of tissue is acquired is known with great precision and the locations recorded by storing each piece individually in the tissue sample cassette 40.

Once the tissue samples 132*a*, 132*b*, 132*c* and 132*d* are loaded into the tissue sample cassette 40, the samples are ready for analysis. FIG. 10 shows an embodiment of the tissue sample cassette 40 which further comprises covers 144 over the chambers 120*a*, 120*b*, 120*c* and 120*d*. Covers 144 contain the tissue samples within the chambers 120 and protect them from outside contamination during transport to the analysis lab. Thus, during the entire process, the tissue samples never have to be handled individually or manually. Additionally, the samples may be processed for examination while in the tissue sample cassette. For example, if the preparation involves impregnating and embedding the tissue samples in paraffin and slicing them into thin sections, this may be performed with the samples in the cassette.

FIGS. 11A and 11B illustrate a first alternate cutting mechanism for the biopsy instrument 10. In this embodiment, a hollow piercing needle 244 has a pointed distal end 245 and a tissue receiving port 246. The hollow piercing needle 244 is movably positioned coaxially within an outer cannular cutter 268. A tubular knock out pin 292 is movably positioned coaxially within the hollow piercing needle 244. As shown by arrows 294 and 296, the outer cannular cutter 268 is capable of rotational motion about the hollow piercing needle 244 as well as translational motion along their common longitudinal axis. The outer cannular cutter 268 rotational motion is controlled by drive motor 56 and the linear motion along the longitudinal axis is controlled by the linear driver 64. A combination of these two actions provides the cutting action necessary to sever a tissue sample which has prolapsed into the tissue receiving port 246. As with the previous embodiment, the knock out pin 292 may provide vacuum to the tissue receiving port to aid in prolapsing the tissue into the chamber as well as to provide a force to hold the severed sample and transport it through the hollow piercing needle to a sample storage area, such as sample cassette 40 (FIG. 2). In some embodiments, the vacuum holds the tissue sample next to a vent hole in the end of the knock out fan pin 292 while the knock out pin is withdrawn, dragging the tissue sample with it. It other embodiments, the end of the knock out pin 292 is open and the tissue sample is suctioned through the hollow interior of the tubular knock out pin 292 into a tissue sample receiving area.

FIGS. 12A and 12B illustrate a second alternate cutting mechanism for the biopsy instrument 10. In this embodiment, a hollow piercing needle 344 has a pointed distal end 345 and a tissue receiving port 346. The hollow piercing needle 344 is movably positioned coaxially within an outer cannular cutter 368 which also has a tissue receiving port 376. In operation, the two receiving ports 346 and 376 are aligned thereby allowing tissue adjacent the ports to prolapse into the hollow interior of the piercing needle 344. As shown by arrow 394, the outer cannular cutter 368 is capable of rotational motion about the hollow piercing needle 344. The outer cannular cutter 368 rotational motion is controlled by cutter drive motor 56. Thus, the tissue which has prolapsed into the interior of the piercing needle 344 is severed by rotating the outer cannular cutter 368 about the piercing needle 344, thereby severing the tissue and closing the tissue receiving port 346. A vacuum source applied to the proximate end of the hollow piercing needle 344 suctions the tissue sample through the hollow interior of the hollow piercing needle 344 into a tissue sample receiving area. Alternately, the inner piercing needle 344 containing the tissue sample may be translated out of the body to the cassette 40 as previously described. Translation is controlled by linear actuator 88.

Figure 13A:
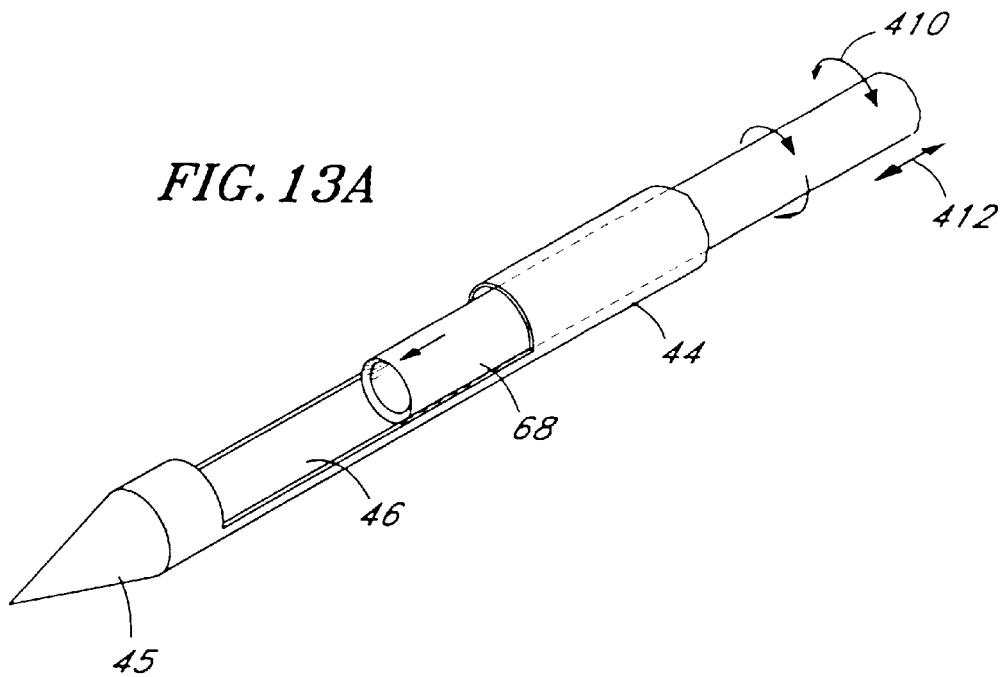
FIGS. 13A, 13B and 13C illustrate an alternate cutting action for the cutting mechanism previously described in connection with FIGS. 1K–6.
Figure 13B:
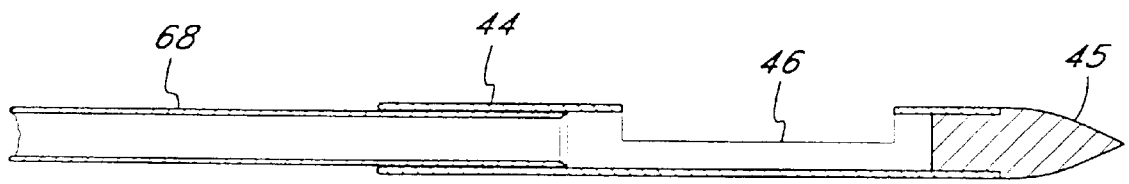
Figure 13C:
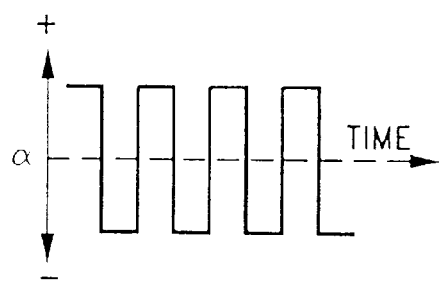

FIGS. 13A, 13B and 13C illustrate an alternate cutting action for the cutting mechanism previously described in connection with FIGS. 1K–6. The cutting action described in FIGS. 1K–6 was a linear slicing of the tissue which had prolapsed into the tissue receiving port 46 by the coaxial linear motion of the cannular inner cutter 68 through the hollow outer piercing needle 44. FIGS. 13A and 13B illustrate the same structure comprising the cannular inner cutter 68 and the hollow outer piercing needle 44. However, the cutting action is modified. As shown by arrows 410 and 412, the cannular inner cutter 68 is capable of rotational motion within the hollow piercing needle 44 as well as translational motion along their common longitudinal axis. The cannular inner cutter 68 rotational motion is controlled by cutter drive motor 80 and the linear motion along the longitudinal axis is controlled by the linear driver 88. A combination of these two actions provides the cutting action necessary to sever a tissue sample which has prolapsed into the tissue receiving port 46. The rotational motion may be continuous or oscillatory, as shown in FIG. 13C. FIG. 13C shows an oscillating pulse pattern for driving the rotary motion of the cutter driver motor 80 first in one direction through a specified angle of rotation followed by rotation in the reverse direction for a specified angle of rotation. In some cases, it has been found that a clockwise rotation of approximately 30 to 40 degrees followed by a counterclockwise rotation of approximately 30 to 40 degrees works well at a frequency of approximately 10 to 40 cycles per second. This action may be achieved with a stepper motor or other type of rotary to oscillating drive mechanism. Likewise, the linear motion along the common longitudinal axis may be linear in one direction or oscillatory. The linear motion is provided by inner cutter linear driver 88 which may be driven by a solenoid for constant linear motion, an ultrasonic transducer or mechanisms referred to above for oscillatory motion or a combination of both. Removal of the severed tissue sample into a tissue receiving area may be by any of the previously described methods.

Figure 14A:
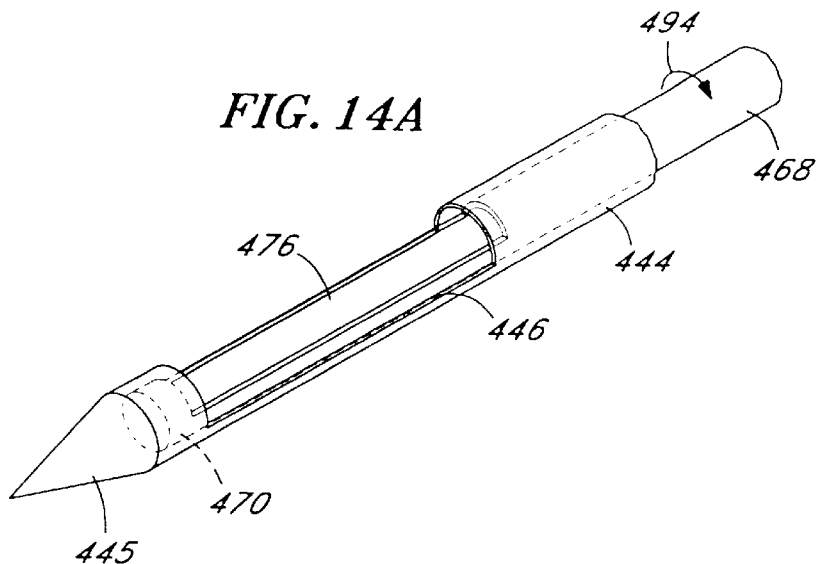
FIGS. 14A, 14B and 14C illustrate a third alternate cutting mechanism for the biopsy instrument having receiving ports in both the piercing needle and the cutter whereby the tissue is severed by rotation of the cutter.
Figure 14B:
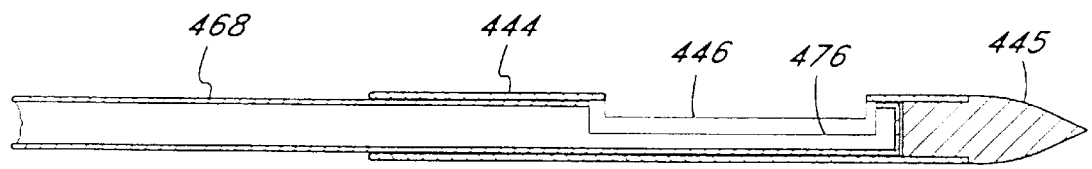
Figure 14C:
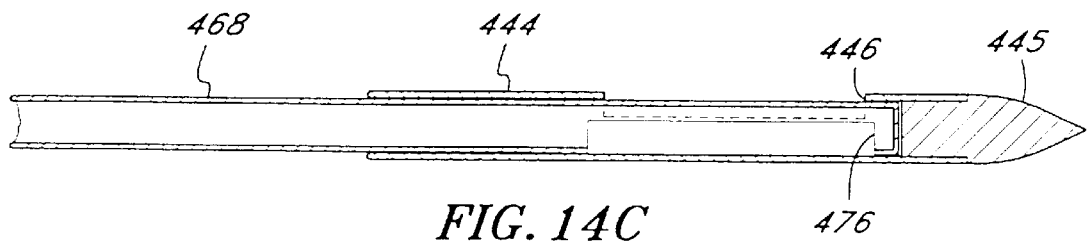

FIGS. 14A, 14B and 14C illustrate a third alternate cutting mechanism for the biopsy instrument 10. In this embodiment, a hollow piercing needle 444 has a pointed distal end 445 and a tissue receiving port 446. An inner cannular cutter 468 having a tissue receiving port 476 is movably positioned coaxially within the hollow piercing needle 444. In operation, the two receiving ports 446 and 476 are aligned thereby allowing tissue adjacent the ports to prolapse into the hollow interior of the inner cannular cutter 468 (FIG. 14B). As shown by arrow 494, the inner cannular cutter 468 is capable of rotational motion within the hollow piercing needle 444. The inner cannular cutter 468 rotational motion is controlled by cutter drive motor 80. Thus, the tissue which has prolapsed into the interior of the inner cannular cutter 468 is severed by rotating the inner cannular cutter 468 about the piercing needle 444, thereby severing the tissue and closing the tissue receiving port 446 (FIG. 14C). The distal end 470 of the inner cannular cutter 468 is closed, thereby containing the severed sample tissue within the cutter while the cutter 468 is withdrawn from the piercing needle 444 to retrieve the sample. In an alternate embodiment, the distal end 470 of the inner cannular cutter 468 is open. Frictional forces or vacuum applied through the tubular knock out pin 92 contain the severed sample within the notch while the cutter 468 is withdrawn from the piercing needle 444 to retrieve the sample.

Figure 15A:
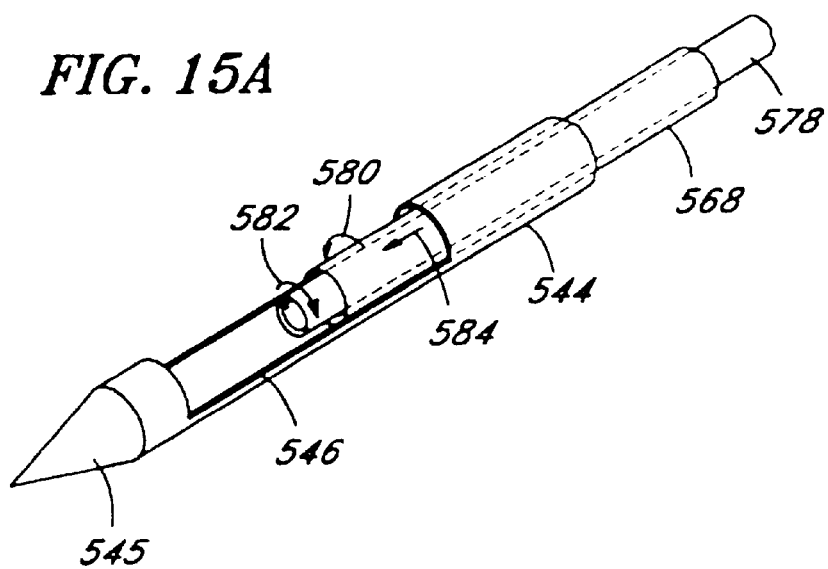
FIGS. 15A and 15B illustrate a fourth alternate cutting mechanism for the biopsy instrument having two counter-rotating inner cutters.
Figure 15B:
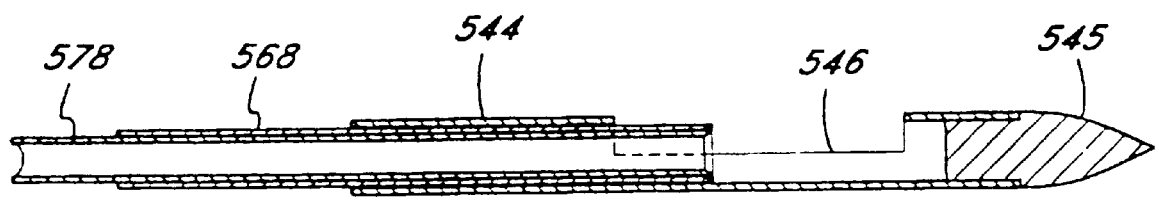

FIGS. 15A and 15B illustrate a fourth alternate cutting mechanism for the biopsy instrument 10. In this embodiment, a is hollow piercing needle 544 has a pointed distal end 545 and a tissue receiving port 546. A first inner cannular cutter 568 is movably positioned coaxially within the hollow piercing needle 544. A second inner cannular cutter 578 is movably positioned coaxially within the first inner cannular cutter 568. In operation, the first inner cannular cutter 568 rotates in a first direction as indicated by arrow 580 and the second inner cannular cutter 578 counter-rotates in the opposite direction as indicated by arrow 582. The rotation of the two inner cannular cutters 568 and 578 is controlled by the two drive motors 80, 104 (FIG. 2). Additionally, the two inner cannular cutters 568 and 578 move axially within the hollow piercing needle 544 as indicated by arrow 584. The axial motion is controlled by linear drivers 88, 112 (FIG. 2). Removal of the severed tissue sample into a tissue receiving area may be by any of the previously described methods.

Figure 16:
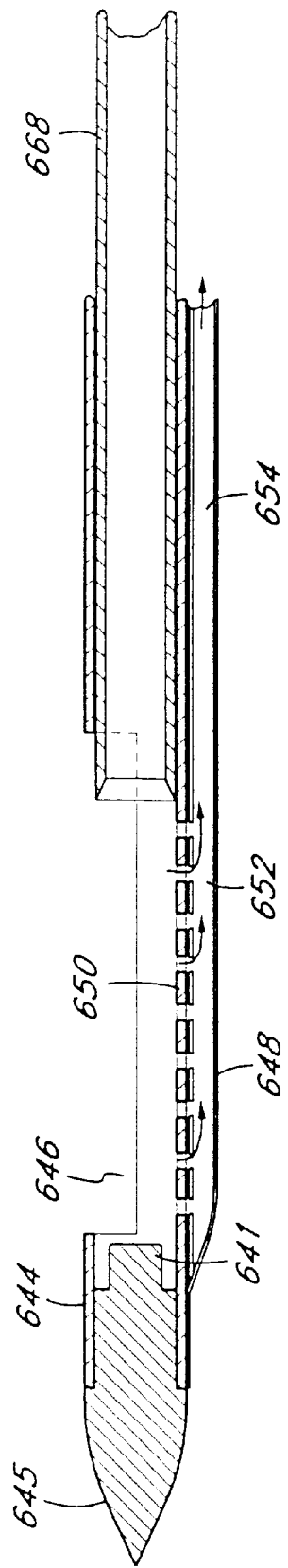
FIG. 16 shows a piercing needle with a tissue receiving port having a vacuum manifold.

FIG. 16 illustrates an embodiment of an outer piercing needle 644 which has a pointed distal end 645, a tissue receiving port 646, and a vacuum manifold 648 adjacent the tissue receiving port. An inner cannular cutter 668 is movably positioned coaxially within the hollow piercing needle 644. The vacuum manifold 648 includes a perforated section 650 having a vacuum chamber 652 on one side and the tissue receiving port 646 on the other side. The vacuum chamber 652 is connected to a vacuum source by a tube 654. In operation, vacuum applied to the manifold 648 is uniformly distributed over the entire receiving port 646 thereby drawing larger and more uniform tissue samples into the port. Severance of the tissue sample in the port from the main tissue mass and transport of the severed tissue to a tissue receiving area may be by several of the methods previously described.

Figure 17:
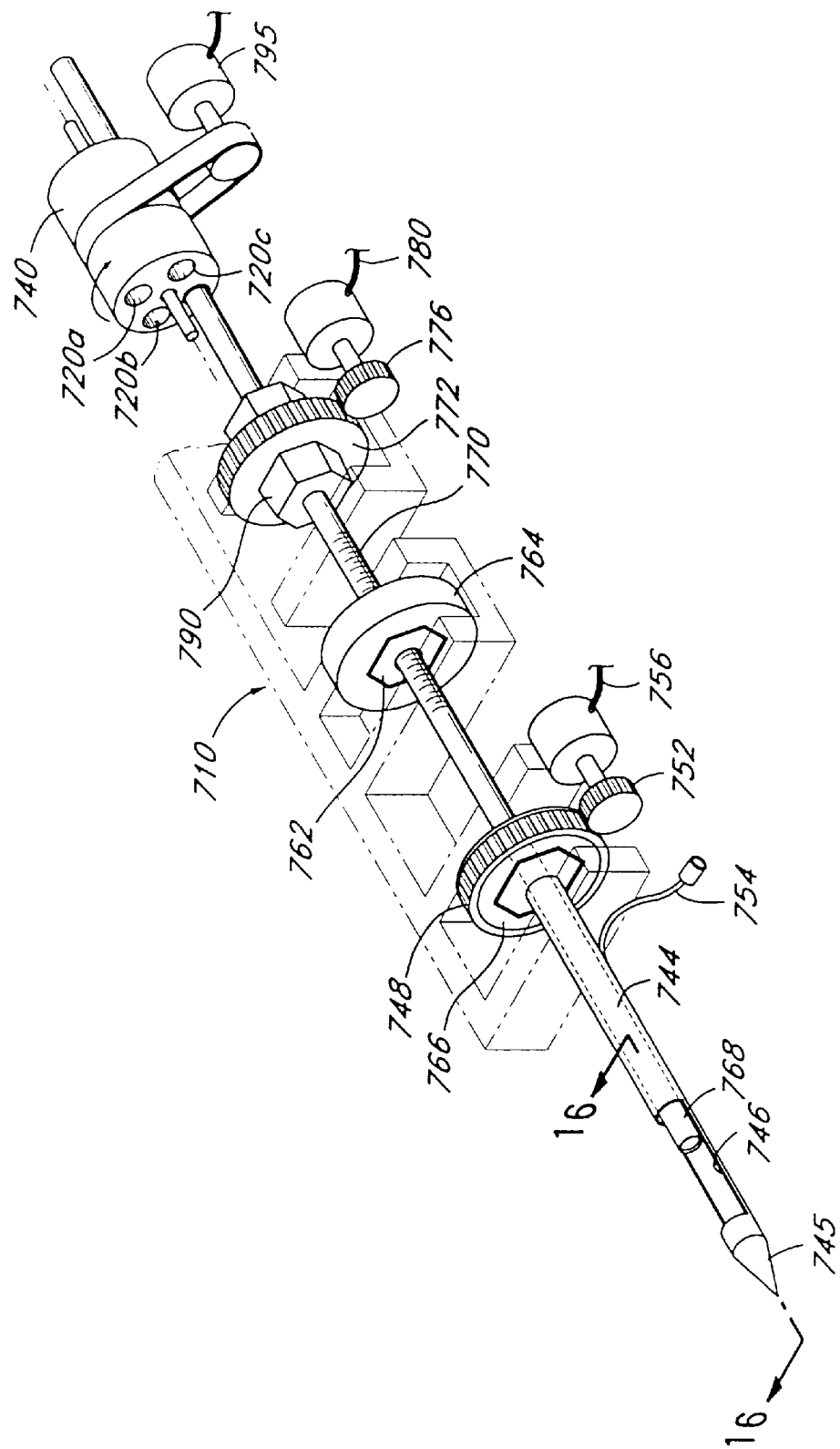
FIG. 17 shows a perspective view of a second preferred embodiment of the biopsy instrument of the present invention.

Shown in FIG. 17 is an alternate embodiment of a biopsy instrument 710 of the present invention. A hollow outer piercing needle 744 having a pointed distal end 745, a tissue sample receiving port 746 and vacuum manifold 754 is mounted to a piercing needle collet 766. Piercing needle collet 766 is mounted in an indexing gear 748. A drive gear 752 driven by a motor 756 meshes with the indexing gear 748. A cannular inner cutter 768 is movably positioned coaxially within the hollow outer piercing needle 744. Threads 770 on the outer surface of cannular inner cutter 768 engage threads in a central hole of a cannular inner cutter collet 762. The collet 762 is mounted in a support 764. A drive collet 790 is also attached to the cannular inner cutter and is mounted in an indexing gear 772. A drive gear 776 driven by a motor 780 meshes with the indexing gear 772. Positioned at a proximate end of the cannular inner cutter 768 is a rotary sample cassette 740 having tissue sample chambers 720. Rotary tissue cassette is belt driven by a drive motor 795.

In operation, the hollow outer piercing needle 744 is positioned within a tissue mass at a location where a sample is desired to be acquired. A vacuum is applied to vacuum manifold 648 as discussed in reference to FIG. 16 to actively draw the tissue into the tissue sample receiving port 746. Drive motor 756 controls the angular position at which the tissue sample receiving port 746 is oriented. Drive motor 780 rotates cannular inner cutter 768 such that it rotates and advances along the common longitudinal axis of the piercing needle 744 and the inner cuter 768 into the sample receiving port 746 thereby severing the tissue sample. The forward motion is induced by the coaction of threads 770 and the collet 762. Removal of the severed tissue sample from the receiving port 746 into a tissue receiving area 720 in cassette 740 may be by any of the previously described methods. Drive motor 795 moves the cassette 740 into position to receive a new sample in another one of the chambers 720.

Figure 18:
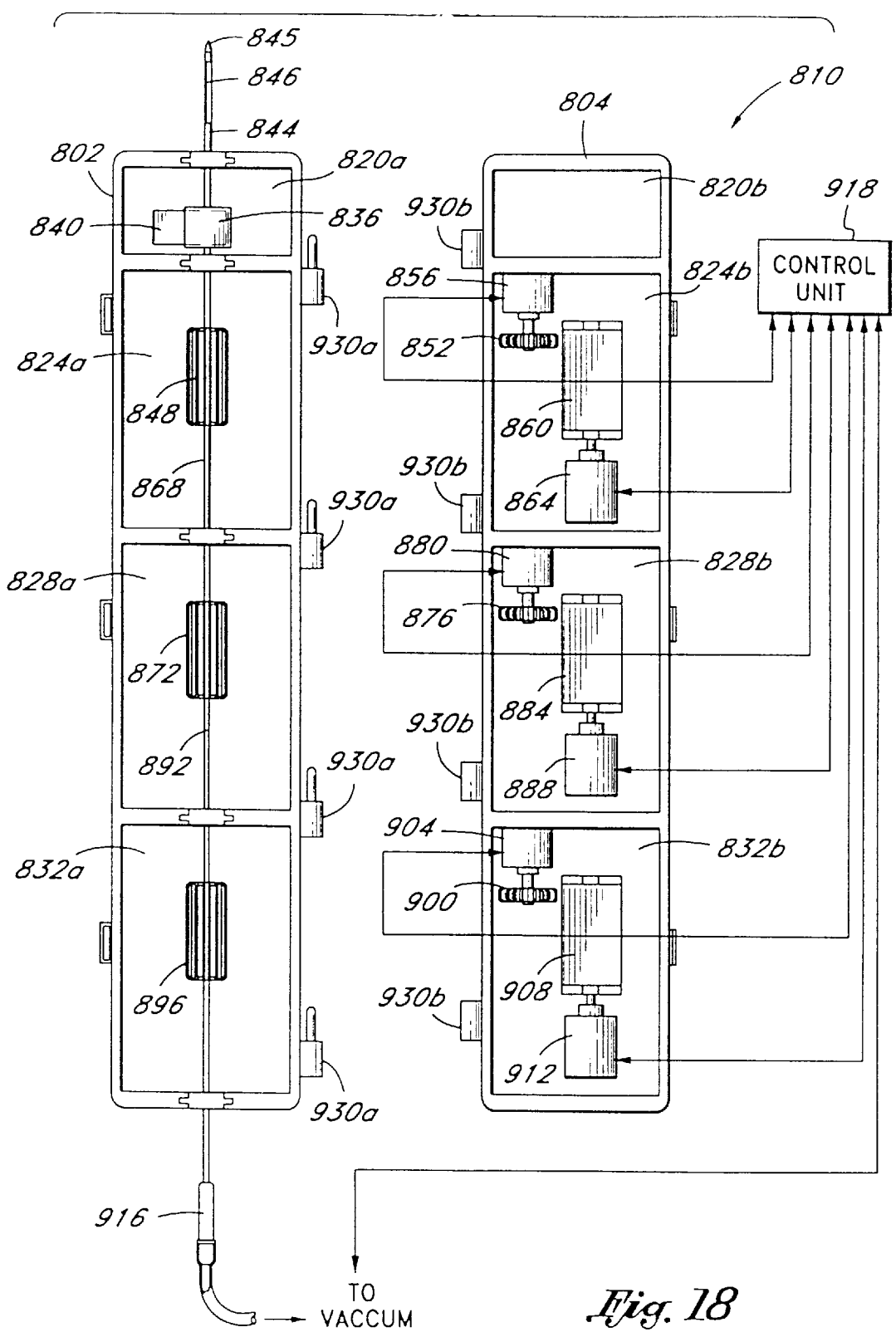
FIG. 18 shows a perspective view of a third preferred embodiment of the biopsy instrument of the present invention.

Another embodiment of the invention is shown in FIG. 18. Biopsy instrument 810 comprises a disposable needle portion 802 and a reusable driver portion 804. The reusable driver portion 804 is divided into four sections including a sample cassette chamber 820b, an outer piercing needle driver chamber 824b, an inner cutter driver chamber 828b and a knock out pin driver chamber 832b. A piercing needle drive gear 852 attached to a piercing needle drive motor 856 is mounted in the outer piercing needle driver chamber 824b along with a piercing needle sliding support 860 and a piercing needle linear driver 864. An inner cutter drive gear 876 attached to an inner cutter drive motor 880 is mounted in the inner cutter driver chamber 828b along with an inner cutter sliding support 884 and an inner cutter linear driver 888. A knock out pin drive gear 900 attached to a knock out pin drive motor 904 is mounted in the knock out pin chamber 832b along with a tubular knock out pin sliding support 908 and a knock out pin linear driver 912. A control unit 918 controls the operation of drive motors 856, 880, 904; linear drivers 864, 888, 912; and a vacuum source connected to a port 916.

The disposable needle portion 802 is divided into four sections including a sample cassette chamber 820a, an outer piercing needle driver chamber 824a, an inner cutter driver chamber 828a and a knock out pin driver chamber 832a. Mounted in the sample cassette chamber 820a is a cassette housing 836 which contains a tissue sample cassette 840. A hollow outer piercing needle 844 is attached to the cassette housing 836 as is an outer piercing needle elongate indexing gear 848. A distal end of the hollow outer piercing needle 844 includes a point 845. Hollow outer piercing needle 844 also includes a tissue receiving port 846. A cannular inner cutter 868 having a cannular inner cutter elongate indexing gear 872 attached to a proximate end is movably positioned coaxially within the hollow outer piercing needle 844. A tubular knock out pin 892 having a tubular knock out pin elongate indexing gear 896 attached to a proximate end is movably positioned coaxially within the cannular inner cutter 868. The vacuum connection 916 is located at a proximal end of tubular knock out pin 892.

The disposable needle portion 802 includes the male side of a pin hinge 930a fixed to one side with the corresponding female side of the pin hinge 930b being fixed to a corresponding side of the reusable driver portion 804. When the disposable needle portion 802 and the reusable driver portion 804 are connected by the pin hinge 930 and folded together, the outer piercing needle elongate indexing gear 848 meshes with the piercing needle drive gear 852 and the outer piercing needle elongate indexing gear 848 is inserted into the piercing needle sliding support 860. Similarly, the cannular inner cutter drive gear 876 meshes with the cannular inner cutter elongate indexing gear 872 and the cannular inner cutter elongate indexing gear 872 is inserted into the inner cutter sliding support 884. Likewise, the knock out pin drive gear 900 meshes with the tubular knock out pin elongate indexing gear 896 and the tubular knock out pin elongate indexing gear 896 is inserted into the tubular knock out pin sliding support 908.

Operation of biopsy instrument 810 after the disposable needle portion 802 and the reusable driver portion 804 have been connected by the pin hinge 930 and folded together is the same as the operation of embodiment 10 as shown in FIGS. 1K–4 and described previously. The separation of driver portion 804 from the needle portion 802 is advantageous in that the needle portion may now be disposed of after use and the driver portion, which does not become contaminated during use and does not require patient contact, can be reused, thereby reducing the cost of the device.

The apparatus and method of the present invention for a Method and Apparatus for Automated Biopsy and Collection of Soft Tissue described herein were developed primarily for breast biopsy. However, the invention may also be useful for other types of biopsies. While the above description comprises embodiments of the invention as applied to breast biopsy, there are other applications which will be obvious to those skilled in the art.

The apparatus and method of the present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

We claim:

1. A biopsy instrument comprising:
   a) a disposable needle portion having:
      i) a needle, said needle having a longitudinal axis, a distal end and a tissue receiving port adjacent to the distal end of said needle; and
      ii) a cutter movably positioned relative to said needle; and
   b) a reusable driver portion having:
      i) a needle linear driver coupled to said needle, such that when said needle linear driver is actuated, said needle advances axially relative to said reusable driver portion for positioning said tissue receiving port of said needle at a biopsy site of the patient; and
      ii) a cutter driver element coupled to said cutter, such that when said cutter driver element is actuated, said cutter moves non-axially relative to said needle for severing a tissue sample received in said tissue receiving port of said needle at the biopsy site;
   wherein said disposable needle portion is separable from said reusable driver portion.

2. The biopsy instrument as recited in claim 1, wherein said reusable driver portion has a needle driver chamber therein containing said needle linear driver, said needle driver chamber receiving said needle so as to couple said needle to said needle linear driver in said needle driver chamber.

3. The biopsy instrument as recited in claim 2, wherein said reusable driver portion has a cutter driver chamber therein containing said cutter driver, said cutter driver chamber receiving said cutter so as to couple said cutter to said cutter driver chamber.

4. The biopsy instrument as recited in claim 1, wherein said needle comprises a piercing needle, said needle distal end being adapted to pierce tissue of a patient.

5. The biopsy instrument as recited in claim 1, wherein said needle is hollow and said cutter is a cannular cutter movably positioned coaxially relative to said needle.

6. The biopsy instrument as recited in claim 5, wherein said disposable needle portion has a knock out element movably positioned coaxially within said cannular cutter.

7. The biopsy instrument as recited in claim 6, wherein said reusable driver portion has a linear driver coupled to said knock out element, and when said linear driver is actuated, said knock out element moves axially distally, and relative to said cannular cutter to facilitate removal of the severed tissue sample received in said tissue discharge port of said needle.

8. The biopsy instrument as recited in claim 1, wherein said reusable driver portion has a needle drive gear coupled to said needle, such that when said needle drive gear is actuated, said needle rotates about the longitudinal axis of said needle relative to said reusable driver portion.

9. The biopsy instrument as recited in claim 1, wherein said cutter driver element comprises a cutter drive gear, such that when said cutter drive gear is actuated, said cutter rotates relative to said needle about the longitudinal axis of said needle.

10. The biopsy instrument as recited in claim 9, wherein said cutter rotates continuously in a single angular direction responsive to actuation of said cutter drive gear.

11. The biopsy instrument as recited in claim 9, wherein said cutter oscillates in opposing angular directions responsive to actuation of said cutter drive gear.

12. The biopsy instrument as recited in claim 1, wherein said reusable driver portion further comprises a cutter linear driver coupled to said cutter, such that when said cutter linear driver is actuated, said cutter moves axially relative to said needle for severing a tissue sample received in said tissue receiving port of said needle at the biopsy site.

13. A method for obtaining biopsy samples from multiple patients, said method comprising:
   a) providing a reusable driver portion of a biopsy instrument having a needle linear driver adapted to couple with first and second needles, and a cutter driver adapted to couple with first and second cutters;
   b) attaching a first disposable portion of said biopsy instrument to said reusable driver portion, said first disposable portion having a first needle coupling with said needle linear driver, and a first cutter coupling with said cutter driver, said first needle having a first tissue receiving port therein;
   c) actuating said needle linear driver to advance said first needle to a first biopsy site of a first patient;
   d) actuating said cutter driver to move said first cutter relative to said first needle for severing a first tissue sample which has entered said first tissue receiving port of said first needle;
   e) removing the first tissue sample from the first patient;
   f) upon removal of all of the tissue samples desired to be taken from the first patient, separating said first disposable portion of said biopsy instrument from said reusable driver portion;
   g) disposing of said first disposable portion of said biopsy instrument;
   h) attaching a second disposable portion of said biopsy instrument to said reusable driver portion, said second disposable portion having a second needle coupling with said needle linear driver, and a second cutter coupling with said cutter driver, said second needle having a second tissue receiving port therein;
   i) actuating said needle linear driver to advance said second needle to a second biopsy site of a second patient;

j) actuating said cutter driver to move said second cutter relative to said second needle for cutting a second tissue sample which has entered said second tissue receiving port of said second needle;

k) removing the second tissue sample from the second patient; and l) upon removal of all of the tissue samples desired to be taken from the second patient, separating said second disposable portion of the biopsy instrument from said reusable driver portion.

14. The method for obtaining biopsy samples from multiple patients as recited in claim 13, wherein said first and second needles are piercing needles for piercing tissue of a patient.

15. A method for obtaining a tissue sample from a patient, said method comprising the steps of:

a) providing a reusable driver portion of a biopsy instrument having a needle linear driver and a cutter driver;

b) providing a disposable needle portion of a biopsy instrument having a needle and a cutter, said needle having a tissue receiving port therein;

c) attaching said disposable needle portion to said reusable driver portion by coupling said needle with said needle linear driver and said cutter with said cutter driver;

d) placing said disposable needle portion in tissue of the patient by advancing said needle with said needle linear driver;

e) severing a tissue sample received in said tissue receiving port of said needle by actuating said cutter with said cutter driver;

f) removing the severed tissue sample from the patient;

g) separating said disposable needle portion from said reusable driver portion; and h) disposing of said disposable needle portion.

16. The method for obtaining a tissue sample from a patient as recited in claim 15, and further comprising the step of reusing said reusable driver portion for a procedure on a second patient.

17. The method for obtaining a tissue sample from a patient as recited in claim 16, including providing another disposable needle portion having a needle and a cutter, said needle having a tissue receiving port therein, said method including repeating steps c) through h) on said second patient with said other disposable needle portion.

* * * * *